US010589098B2

(12) United States Patent
Jung

(10) Patent No.: US 10,589,098 B2
(45) Date of Patent: *Mar. 17, 2020

(54) SYSTEM AND METHOD FOR NEUROMORPHIC CONTROLLED ADAPTIVE PACING OF RESPIRATORY MUSCLES AND NERVES

(71) Applicant: Ranu Jung, Coral Gables, FL (US)

(72) Inventor: Ranu Jung, Coral Gables, FL (US)

(73) Assignee: The Florida International University Board of Trustees, Miami, FL (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/842,956

(22) Filed: Dec. 15, 2017

(65) Prior Publication Data
US 2018/0117334 A1    May 3, 2018

Related U.S. Application Data

(63) Continuation of application No. 14/676,986, filed on Apr. 2, 2015, now Pat. No. 9,872,989.

(51) Int. Cl.
*A61N 1/36* (2006.01)
*A61N 1/372* (2006.01)
(52) U.S. Cl.
CPC ....... *A61N 1/36139* (2013.01); *A61N 1/3601* (2013.01); *A61N 1/3611* (2013.01); *A61N 1/37217* (2013.01)
(58) Field of Classification Search
CPC .................................................. A61N 1/3601
See application file for complete search history.

(56) References Cited

U.S. PATENT DOCUMENTS

| 8,790,282 B2 | 7/2014 | Jung et al. |
| 2013/0030497 A1 | 1/2013 | Karamanoglu et al. |
| 2015/0213191 A1 | 7/2015 | Abdelghani et al. |

OTHER PUBLICATIONS

Botros, S.M. et al., "Neural Network Implementation of a Three-Phase Model of Respiratory Rhythm Generation," Biological Cybernetics, 1990, 63(2):Abstract.
(Continued)

*Primary Examiner* — Carl H Layno
*Assistant Examiner* — Jennifer L Ghand
(74) *Attorney, Agent, or Firm* — Saliwanchik, Lloyd & Eisenschenk

(57) ABSTRACT

Adaptive systems and methods for automatically determining and continuously updating stimulation parameters for adjusting ventilation to accommodate a patient's specific physiology, metabolic needs, and muscle state are disclosed herein. Having a closed loop implementation, the system may comprise a controller including a neuromorphic controlled adaptive feed-forward Pattern Generator/Pattern Shaper (PG/PS) assembly, which controls respiratory muscle movement using electrical stimulation. This PG/PS assembly comprises a biomimetic design where the pattern generator includes a neural network mimicking the simplified connectivity pattern of respiratory related neurons in the brain stem to produce a rhythmic breathing pattern frequency and the pattern shaper includes a neural network mimicking the simplified connectivity pattern of neurons to produce a stimulus control signal. This biomimetic design for the controller automatically customizes and continually updates stimulation parameters to achieve a desired breathing pattern and, thereby, slow the development of muscle fatigue.

20 Claims, 8 Drawing Sheets

(56) References Cited

OTHER PUBLICATIONS

Hawkins, David et al., "Muscle Force as Affected by Fatigue: Mathematical Model and Experimental Verification," Journal of Biomechanics, Sep. 1993, 26(9):1117-1128.
Levine, Sanford et al., "Cellular Adaptations in the Diaphragm in Chronic Obstructive Pulmonary Disease," New England Journal of Medicine, 1997, 337:1799-1806.
Macklem, P.T. et al., "A Model of Inspiratory Muscle Mechanics," Journal of Applied Physiology, Aug. 1, 1983, 55 (2):Abstract.

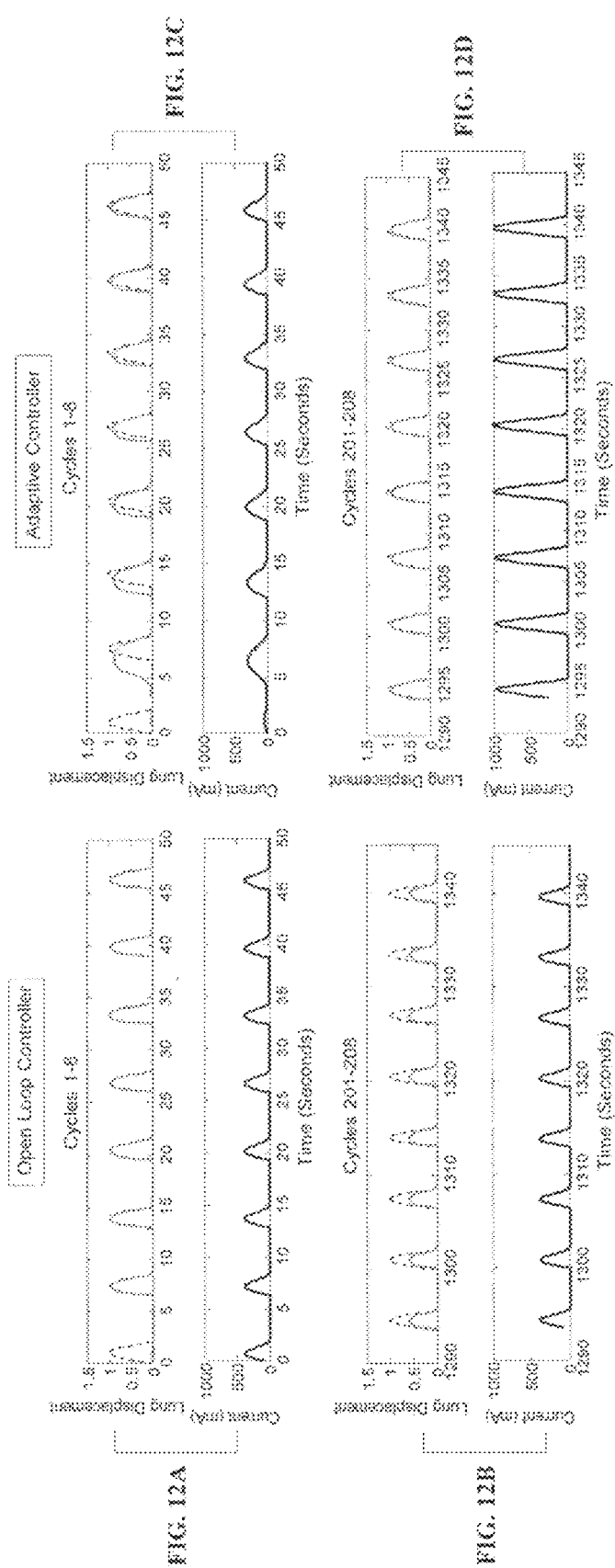

SYSTEM AND METHOD FOR NEUROMORPHIC CONTROLLED ADAPTIVE PACING OF RESPIRATORY MUSCLES AND NERVES

CROSS-REFERENCE TO RELATED APPLICATION

This application is a continuation application of U.S. application Ser. No. 14/676,986, now U.S. Pat. No. 9,872, 989, filed Apr. 2, 2015, which is hereby incorporated by reference in its entirety, including any figures, tables, and drawings.

GOVERNMENT SUPPORT

This invention was made with government support under NS086088 awarded by the National Institutes of Health. The government has certain rights in the invention.

BACKGROUND OF INVENTION

Ventilation assist devices may be required for patients suffering from Spinal Cord Injuries (SCI) and brain injuries. In particular as a result of trauma or disease, SCI account for 40 cases per million in the United States, according to the National Spinal Cord Injury Statistical Center (NSCISC, 2014). Approximately 276,000 Americans (0.1% of the US population) are SCI survivors, with 12,500 new injuries in the US being reported each year. Signs and symptoms experienced by a patient will vary depending on where the spinal cord is injured and the extent of the injury. It will also depend upon which part of the body that the injured area of the spinal cord innervates. In particular, injury to the spinal cord can cause problems with voluntary motor control of a myotome (a group of muscles innervated through a specific part of the spinal cord). The muscles may contract uncontrollably, become weak, or be completely paralyzed. The loss of muscle function can have additional effects when the muscle is not used, including disuse atrophy of the muscle and bone degeneration. Fortunately, many cases of disuse atrophy can be reversed with exercise.

The most common site of injury occurs in the cervical cord (representing 54% of all cases), which may lead to partial or complete tetraplegia, also known as quadriplegia. Damage to the cervical spinal cord may also lead to depreciated functioning of the primary muscle for breathing—the diaphragm (a thin sheet of muscle supporting the lungs and separating the thoracic cavity containing the heart and lungs, from the abdominal cavity). This depreciated functioning of the diaphragm is due to the impact of the injury upon the nerves supplied to the diaphragm from the phrenic motor neurons in the damaged cervical spinal cord. In particular, the phrenic nerve stems from cervical spinal nerve roots C3, C4, and C5, which innervate the diaphragm, and thereby, enable breathing. Under normal functioning, as the diaphragm contracts, the volume of the thoracic cavity increases and air is drawn into the lungs. If the spinal cord is contused above cervical spinal nerve root C3, then spontaneous breathing may be not possible. Accordingly, people with high-level cervical SCI may also have partial or complete loss of ventilatory control because of diaphragmatic paralysis.

Ventilation may also be further impaired due to paralysis of the external intercostal muscles, which help to expand and stabilize the rib cage during breathing. Additionally, the paralysis of the abdominal muscles, which sometimes are engaged for active expiration, or internal intercostal muscles used for forceful exhalation such as coughing or under exercise may also impair ventilation. Both sets of these muscles are innervated by motor neurons that are distributed across the thoracic (chest) region of the spinal cord (levels T1 to T11). To further complicate the consequences of SCI, diseases of the respiratory system are the leading cause of death after a SCI according to the NSCISC, where, 66.9% of these reported deaths resulted from pneumonia.

Most people with paralysis of the respiratory muscles require ventilation management and are initially supported using positive pressure-mechanical ventilation, where air (or another gas mix) is pumped through a tube inserted into the mouth and down into the trachea. However, this form of assisted mechanical ventilation is associated with significant discomfort, diaphragm atrophy, atelectasis, and barotrauma. In particular, the use of a mechanical ventilator may sometimes cause the muscles of the diaphragm to atrophy, which can occur after as little as 18 to 69 hours of complete diaphragmatic inactivity. Further, as a result of diaphragm atrophy, autonomous respiratory recovery is delayed. Moreover, the patient may become dependent upon the use of a mechanical ventilator, causing the muscles of the diaphragm to fatigue quickly without ventilation assistance, thereby making it difficult for the patient to breathe on their own for an extended period of time.

Fortunately, diaphragmatic pacing through electrical stimulation of the diaphragm may eliminate muscle atrophy, where laparoscopic implantation of intramuscular electrodes is used to stimulate the diaphragm. Particularly, diaphragmatic pacing in both adults and children can help wean patients off the mechanical ventilator, since diaphragmatic pacing has been proven to strengthen the diaphragm. Diaphragmatic pacing may also be beneficial for patients with central alveolar ventilation (sleep apnea) and Chronic Obstructive Pulmonary Disease (COPD). However, electrical stimulation of the diaphragm causes the diaphragm muscles to fatigue quickly. As such, diaphragmatic pacing through electrical stimulation not only limits the time off of the mechanical ventilator, but also does not allow enough time for therapeutic strengthening of the muscles of the diaphragm. In the alternative, electrical stimulation of the phrenic nerve for diaphragm pacing has been clinically accepted as an alternative for ventilator-dependent people with tetraplegia. Yet, for patients without intact phrenic nerves or unilateral phrenic function, clinicians must resort to laparoscopic implantation of intramuscular electrodes to stimulate the diaphragm.

Commercially available diaphragmatic pacing systems developed to-date employ an open-loop ventilatory control system to deliver electrical impulses through the implanted electrodes. Despite being widely used, however, open-loop control systems possess time consuming iterative manual tuning of stimulation parameters, which does not compensate for reduced diaphragmatic contraction due to muscle fatigue. Further, the current diaphragmatic pacing systems cannot respond to unanticipated changes or episodes of high metabolic demand, where metabolic demand represents the amount of oxygen necessary for the heart to convert chemical energy into mechanical work.

BRIEF SUMMARY

Adaptive systems and methods for automatically determining and continuously updating stimulation parameters for adjusting ventilation to accommodate a patient's specific physiology, metabolic needs, and muscle state are disclosed herein. One example of an adaptive system may comprise at least one electrode implanted in at least one muscle or nerve of the user and a first feedback section including at least one sensor for detecting at least one physiological parameter of the user. The adaptive system may further comprise a controller that generates a stimulus control signal for adjusting the breathing pattern using a first difference between the at least one detected physiological parameter and a desired physiological parameter; wherein, the controller sends the stimulus control signal to the at least one electrode for controlling the movement of the at least one muscle or nerve.

The controller may comprise a feed-forward section for generating at least one stimulus control signal for adjusting the breathing pattern using the first difference. The feed-forward section may include a pattern generator coupled between a first comparator and a pattern shaper, where the first comparator generates the first difference. The pattern generator may comprise a biomimetic design having a neural network mimicking the simplified connectivity pattern of respiratory related neurons in the brain stem to produce a breathing pattern frequency, which is based upon the first difference between the detected and desired physiological parameters. The pattern shaper may comprise a biomimetic design having a neural network mimicking the simplified connectivity pattern of phrenic motorneurons that determine at least one frequency of stimulation (number of times the stimulation pulses occur) for stimulating the at least one muscle or nerve and the amplitude of at least one stimulation pulse associated with this stimulation, based upon the breathing pattern frequency.

The adaptive system may further comprise a second feedback section including at least one lung volume sensor for detecting the lung volume. In addition, the controller may further comprise a lung volume section that generates a desired normalized lung volume based upon the difference between the at least one detected physiological parameter of the user and a desired physiological parameter of the user. The lung volume section may also generate a second difference between the desired normalized lung volume and the detected lung volume, wherein the second difference may be used to adaptively control the neural network of the pattern shaper. In response, the pattern shaper can generate the stimulus control signal and send this signal to the at least one electrode to adjust at least one muscle and/or nerve. In another embodiment, the second difference may be used to adaptively control the neural network of the pattern generator, wherein, the pattern generator generates a corresponding breathing pattern frequency.

The biomimetic design of the pattern generator circuit is based on knowledge of connectivity of respiratory related neurons in the brain stem of mammals, which makes it a "neuromorphic" design, or a design that mimics neurobiological architectures present in the nervous system. The system may include an electronic circuit made from analog Very Large Scale Integrated (VLSI) components and discrete electronic components capable of autonomously generating cyclic voltage output. A power supply may serve the controller and adaptive system.

By achieving more efficient ventilation, the control system may also slow the development of muscle fatigue, thereby extending the periods of time off the mechanical ventilator.

BRIEF DESCRIPTION OF DRAWINGS

FIGS. 12A-D show graphical charts of the comparison of desired versus measured values in both an open loop controller and an adaptive controller, where the lung displacement and current supplied to the muscle are illustrated.

DETAILED DESCRIPTION

Adaptive systems and methods for automatically determining and continuously updating stimulation parameters for adjusting ventilation to accommodate a patient's specific physiology, metabolic needs, and muscle state are disclosed herein. One example of an adaptive system may comprise at least one electrode implanted in at least one muscle or nerve of the user and at least one sensor for detecting at least one physiological parameter of the user. The adaptive system may further comprise a controller that generates a stimulus control signal for adjusting the breathing pattern using at least one detected physiological parameter; wherein, the controller sends the stimulus control signal to the at least one electrode for controlling the movement of the at least one muscle or nerve.

The controller may comprise a pattern generator coupled to a pattern shaper, where the pattern generator comprises a biomimetic design having a neural network mimicking the simplified connectivity pattern of respiratory related neurons in the brain stem to produce a rhythmic breathing pattern frequency. The pattern shaper may comprise a biomimetic design having a neural network mimicking the simplified connectivity pattern of phrenic motorneurons in the spinal cord that determine the stimulation pattern, including the amplitude of at least one simulation pulse and frequency of stimulation (number of times the stimulation pulses occur) for stimulating the at least one muscle or nerve, based upon the rhythmic breathing pattern frequency. The pattern shaper may produce a stimulus control signal, having the amplitude and frequency of at least one simulation pulse, which may be sent to the at least one muscle or nerve.

The adaptive system may further comprise at least one lung volume sensor to be used to derive a second control signal for adapting the pattern shaper, which can adjust the lung volume to a desired lung volume trajectory. In particular, the controller may comprise a feed-back section that generates a desired normalized lung volume based upon the difference between the at least one detected physiological parameter of the user and a desired physiological parameter of the user. The controller may also include another feedback section that generates a pattern shaper control signal based upon the difference between a sensed lung volume and a desired normalized lung volume. In response, the pattern shaper generates and sends a second stimulus control signal to the at least one electrode to adjust the lung volume to the desired lung volume.

By achieving more efficient ventilation, the control system may also slow the development of muscle fatigue, thereby extending the periods of time off the mechanical ventilator. Accordingly, the use of adaptive control strategies in respiratory pacing systems can simplify initial setup procedures and all the system to adjust stimulation values to account for changes due to muscle fatigue and/or respiratory demand.

Figure 1:
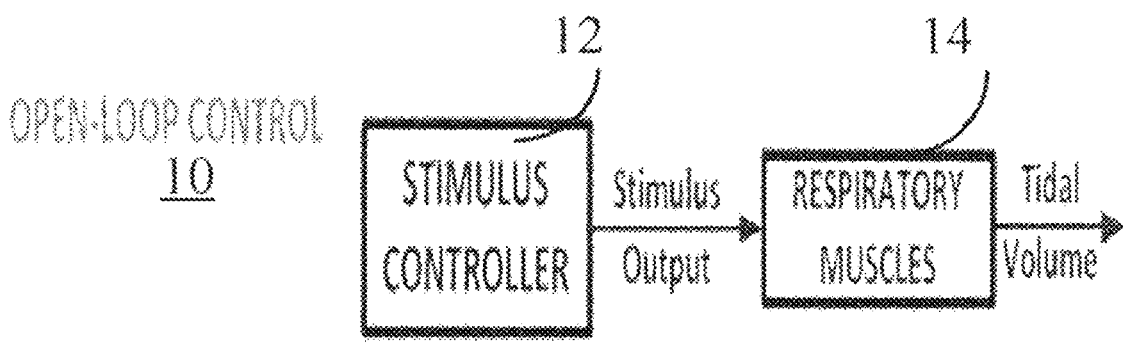
FIG. 1 illustrates an example of an open loop control system for respiratory ventilation.

FIG. 1 illustrates an example of an open loop control system for respiratory ventilation. The system may comprise a stimulus controller 12 coupled to at least one respiratory muscle 14. In operation, the stimulus controller 12 sends signals to implanted intramuscular electrodes (not shown) to stimulate the inspiratory respiratory muscle 14 to contract; as a result, the tidal volume of the lungs is increased. Tidal volume can help to ensure adequate ventilation without causing trauma to the lungs. Tidal volume is measured in milliliters, while ventilation volumes may be estimated based on a patient's ideal body mass.

Most commercially available diaphragmatic pacing systems developed to-date employ this open-loop ventilatory control system to deliver electrical impulses through the implanted electrodes. Despite being widely used, open-loop control systems have three major drawbacks. First, the need for iterative manual tuning of stimulation parameters for each patient requires several extensive sessions. These stimulation parameters include pulse duration, burst width and frequency. For example, stimulation parameters (for diaphragmatic muscles) of lung ventilation response in a human may include a train of pulses at a pulse duration of 50 μs and a frequency of 20 Hz, for a inspiratory burst width of 1 s and repeated every 3 seconds to achieve 20 breaths/minute. Second, the fixed stimulation pattern cannot compensate for reduced diaphragmatic contraction due to muscle fatigue. Third, the open-loop controller cannot respond to unanticipated changes or episodes of high metabolic demand and supply of the heart, which corresponds to the amount of oxygen delivered to the heart and the amount of oxygen extracted therefrom. Additionally, these commercially available diaphragmatic pacing systems are not used to target the extra-diaphragmatic muscles (i.e. intercostals and abdominal muscles). Although in these systems electrical stimulation eliminates muscle atrophy, the electrical stimulation causes diaphragmatic muscle fatigue.

In particular, three companies, Synapse Biomedical Inc., Avery Biomedical Inc., and Arotech, already have open-loop stimulators on the market for diaphragmatic/phrenic pacing. None of their devices, however, account for fatigue of the diaphragm over a long duration of stimulation. Additionally, when open-loop stimulation is performed, considerable effort must be employed to develop stimulator parameters that will yield the desired lung volume displacement profile. This process is time consuming, laborious, and costly.

Figure 2:
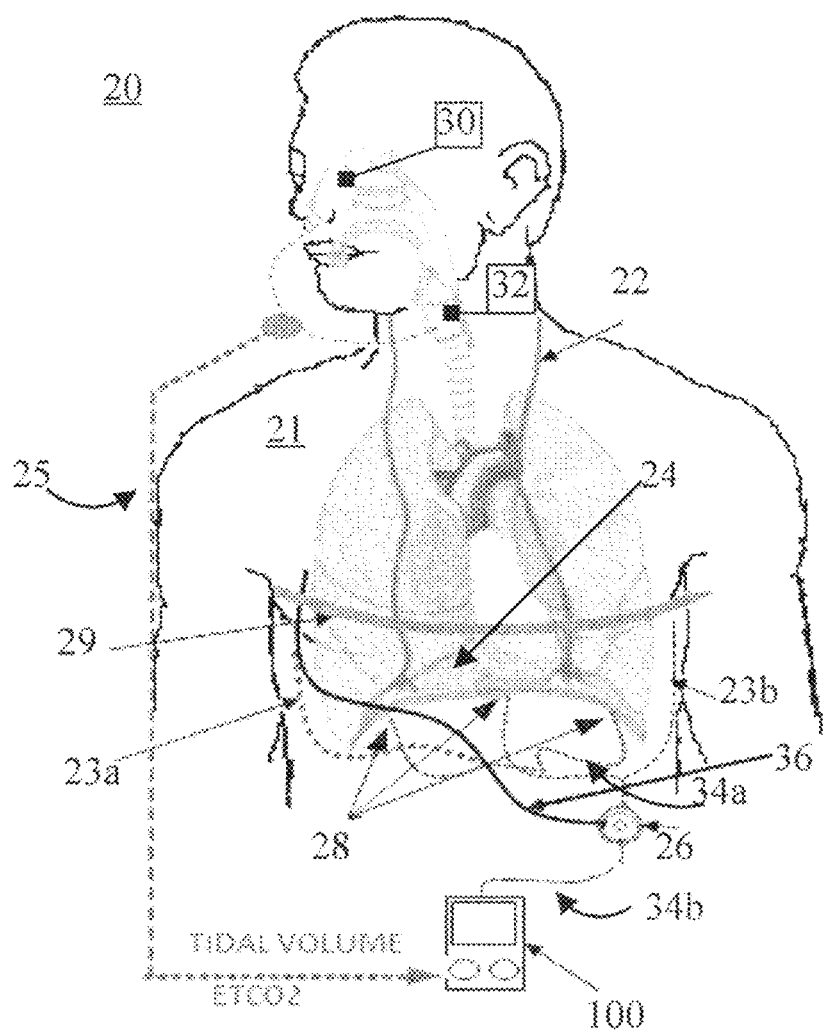
FIG. 2 illustrates a block diagram of a first example of an adaptive system for pacing of respiratory muscles and nerves using neuromuscular stimulation.

FIG. 2 illustrates a block diagram of a first example of an adaptive neuromorphic system 20 for pacing of respiratory muscles and nerves using neuromuscular stimulation. The adaptive ventilation system 20 may comprise a well-tuned closed-loop ventilatory controller 100 for successful breathing rehabilitation in the case of diaphragm muscle atrophy. In an example embodiment, system 20 uses electrical stimulation to eliminate muscle atrophy, while minimizing diaphragmatic muscle fatigue. In particular, the exemplary, adaptive control system 20 provided herein may provide appropriate and customized electrical stimulation of the inspiratory muscles (diaphragm 24 and external intercostal (not shown)) and expiratory muscles (internal intercostals and abdominal muscles) (not shown) for natural and efficient ventilatory assist and for rehabilitation therapy of the muscles to prevent disuse atrophy. Stimulation of extra-diaphragmatic respiratory muscles, including the external upper intercostals for inspiration and the abdominal muscles for expiration, in an optimal sequence can stabilize the rib cage to avoid movement during diaphragmatic pacing. Thereby, ventilation can be enhanced and made more efficient. In the alternative, the adaptive controller may also stimulate the phrenic and intercostal nerves in conjunction with or in lieu of the electrical stimulation of the inspiratory and expiratory muscles.

The adaptive ventilation system 20 may comprise a controller 100 coupled to electrodes 28, which stimulate respiratory muscles 24 and/or electrodes which stimulate the phrenic nerve 22 within a user 21. This system 20 may provide an integrated control system, in that a neuromorphic controller 100 provides control of the respiratory muscles 24 based on principles of the architecture and function of brain stem neurons for control of rhythmic movement; wherein, the controller 100 senses and controls the breathing pattern of the user through the use of a pattern generator/pattern shaper (PG/PS) controller model, as described in further detail with reference to FIG. 4. In operation, the stimulation of the muscles may occur through the use of electrodes 28 implanted into or on the muscles to activate the neuromuscular junction. The electrodes 28 may comprise electrodes of varying types, including but not limited to epimysial electrodes or intramuscular electrodes.

In a first embodiment, the electrodes may be implanted in the body in relative proximity to the diaphragm 24 and directly coupled to the external stimulus controller 100, as shown in FIG. 2. This external stimulus controller 100 may couple to a power supply and fit within a belt pouch or back pack (not shown). In a second embodiment, the stimulation may be directed to specific nerves innervating the muscles or ventral roots preceding from these nerves. For example, the phrenic nerve 22 innervating the diaphragm 24 may be stimulated by the implanted electrodes. Additionally, the thoracic intercostal nerves (not shown) innervating the external and internal intercostal and abdominal muscles may be stimulated by the implanted electrodes (23a, 23b). These electrodes may be extraneural (e.g. cuff) electrodes or intraneural (e.g. longitudinal intrafascicular electrodes). These electrodes may comprise a wireless communication module that supports wireless communication, such as Radio Frequency (RF) communications using Bluetooth™, though embodiments are not limited thereto.

The coupling of the external stimulus controller 100 to the diaphragmatic muscle 24 or phrenic nerve 22 may be through a communication channel (34a, 34b), where data and signals are transferred between the stimulus controller 100 and diaphragm 24 or phrenic nerve 22 through the communication channel (34a, 34b) and communication link 26. The data and signal information transferred through the communication channel (34a, 34b) are generally in the form of electrical communication signals. In one embodiment, the communication channel (34a, 34b) may be a wired or wireless network, or any variety of other communication links. Communication channel (34a, 34b) carries signals and can be implemented using a variety of wired or wireless communication means including wire or cable, fiber optics, conventional phone line, cellular phone link, wireless data communication link, RF link (such as Bluetooth™) or infrared link, though embodiments are not limited thereto. For example, the electrodes 28 may comprise one or more remote electrodes that wirelessly communicate with the controller 100. In the alternative, the electrode may be coupled to an implanted wire that couples to an external stimulus controller 100.

In operation, the controller 100 sends a signal to the diaphragm 24, instructing it to contract or to drop down. When the signal is sent to the diaphragm 24, the diaphragm 24 contracts and the chest cavity increases, where the lungs expand to fill with air. When the signal ceases or falls to 0 V, the diaphragm 24 springs back into position, decreasing the chest cavity, expelling air out.

The adaptive ventilation system 20 may further comprise sensors 30 coupled to the user 21 that detect physiological parameters, such as End Tidal carbon dioxide ($ETCO_2$), arterial $CO_2$, and oxygen levels. The system 20 may further comprise sensors 32 that detect lung volume. These sensors 30 may be associated with or mounted on the controller 100, or in or on the body 21. Several types of sensors may be used to transmit physiological information. The sensors 30 are interconnected with the stimulus controller 100 and may provide accurate information about the transthoracic impedance between external or internal electrodes, chest or abdominal wall motion, phrenic nerve activity, blood pH, blood oxygen concentration, blood carbon dioxide concentration, blood pressure, activity level and/or body posture using an accelerometer, phrenic nerve activity, airflow, heart sounds, sensed electrical activity, blood flow, and/or blood circulation time.

Specifically, a first type of sensor can be provided in or adjacent the nasal cavity or trachea. As shown in FIG. 2, the sensor 30 is illustrated mounted adjacent the nasal cavity. More specifically, the physiological sensors 30 optionally include sensors for minute ventilation in the patient to sense minute ventilation, which is defined as the total volume of air that moves in and out of a user's lungs in a minute. Signals generated by the minute ventilation sensor are passed to the controller 100 for analysis in determining whether to adjust the diaphragmatic pacing rate. Sensor 30 may include a capnograph, or carbon dioxide analyzer, that can be used to assess the percentage of $CO_2$ present in expired air. The concentration of $CO_2$ in expelled air can serve as an indirect measure for metabolism. Normal levels of the partial pressure of $CO_2$ at the end of complete expiration during a breath (the end-tidal $pCO_2$) may be, for example, 5% and 35-45 mmHg (in terms of concentration, 5 to 6%). Accordingly, the capnogram signal can function as an input into the closed loop system 20 that adapts the respiratory cycle duration to the metabolic demand; wherein, the frequency of the pattern generator within controller 100 can be adjusted if the desired percentage of the end-tidal $CO_2$ increases and/or decreases (to be explained further in detail with reference to FIG. 4). Further, since the capnograph can provide a continuous signal, it can also be used to determine respiratory rate. The airflow being sampled may be close to the exhalation site, which may be sampled using an intubation tube (not shown) or a sensor 30 located in from the nasal cavity as shown.

Further, a second type of sensor 32 may include a respiration sensor internal to the ventilator, or a respiration sensor external to the ventilator, such as an intra-tracheal airway sensor 32 as shown. In operation, the controller 100 monitors the signals for indications of the user's activity status through communication channel 25 that couples between sensors 30, 32 and stimulus controller 100. Thereby, the activity of the user 21 may be monitored which impacts the metabolic demand of the heart. For example, when the user 21 is climbing upstairs or descending downstairs, the metabolic demand of the heart changes to an increased rate of oxygen necessary to function. Thereby, the adaptive system 20 may adjust the diaphragmatic pacing to account for the change in metabolic demand.

A third type of sensor 36 can be provided to sense the breath volume, thereby providing real-time feedback of physiological parameters of the user 21 to the controller 100. The system 20 uses the breath volume to assess respiratory muscle performance and lung ventilation. This third sensor type 36 may be mounted anywhere along the thoracic region. The actual breath volume can be obtained by integrating respiratory flow measured using a pneumotachometer (not shown), or directly using a sensor such as a respiratory belt 29 that wraps around the chest and connects to an implanted chest movement sensor 36. In particular, the respiratory belt 29 measures chest expansion and relaxation during breathing through the use of a piezoelectric based sensor and can be used to provide feedback to the adaptive system 20. The belt 29 may comprise a circumferential elasticated band. In the alternative, when using the pneumotachometer, the user 21 may breathe in and out through a tube (not shown) connected to the pneumotachometer. The pneumotachometer is a transducer for measuring the instantaneous flow of respiratory gases, and is useful for measuring expired air flow. The pneumotachometer may comprise a hardware-based integrator that enables online processing of an air flow signal into volume with minimal latency; where, the air flow signal is used to determine the breath volume and may be derived from the rate at which air enters and exits the pulmonary airway. In the alternative, the pneumotachometer may comprise an Analog to Digital converter and a computer program that mathematically integrates the signal to obtain the instantaneous breath volume. This system may use a Fleisch-type pneumotachometer. In still another approach, shoulder movement during breathing may be imaged and used to remotely determine breath volume and flow rate.

There are various other types of sensors that may be used, including but not limited to a sensor placed between intercostal muscles to assess ventilatory rate, an accelerometer or hall effect sensor (to sense movement), an ultrasonic breathing monitoring device (to quantify breathing activity), an ultrasonic proximity sensor, a temperature sensor, a piezoresistive fabric sensor (to measure respiratory rate), an impedance pneumography (to measure respiratory rate), an ultrasonic contactless sensor (for breathing monitoring), and an electromyogram. In the case of electromyograms, implanted electrodes in the diaphragm and/or the internal and external intercostal muscles could also give information about the contraction of these muscles. The electrodes could be hook-like wire electrodes or surface electrodes. For intercostal muscles, the electrodes may be positioned outside; yet, for diaphragmatic EMG, esophageal electrodes may be used. A laparoscopic approach could also be utilized to place the diaphragmatic EMG electrodes.

Advantageous characteristics of sensors 30, 32, and 36 used in the system 20 may be their low-profile, light weight, simple power requirements, fast response times, and low susceptibility to noise. The detection signal provided by sensor 30 may be used to provide information to the neuromorphic controller 100, for detection of real-time physiological changes of the user 21. While only the first type of sensor may be required in certain embodiments of adaptive system 20, the additional aforementioned sensor types are also advantageous to improve the feedback control provided by the system 20. Sensors may alternatively be located on or in the user's body, or mounted on an external backpack. The output of the sensing electrodes will be processed through the electronic circuitry to provide the appropriate voltage or current analog or digital input to the pattern generator.

In another embodiment, the external stimulus controller 100 may couple to the phrenic nerve 22, whereby an electrode, implanted in the body in relative proximity to the phrenic nerve, couples to the nerve 22. The coupling of the external stimulus controller 100 to the phrenic nerve 22 may be wired or wireless. In particular, one or more communication channels may couple between the external stimulus controller 100 and the phrenic nerve 22, through link 26 and communication channel 34b for carrying signals there between. The one or more communication channels can be implemented using a variety of wired or wireless communication means including but not limited to wire or cable, fiber optics, conventional phone line, cellular phone link, wireless data communication link, RF link (such as Bluetooth™) or infrared link. In operation, the controller 100 may send an activation signal to the phrenic nerve 22, which sends a signal to the diaphragm 24. This activation signal may instruct the diaphragm 24 to contract or to drop down. When the diaphragm 24 contracts, the chest cavity increases and the lungs expand to fill with air. When the activation signal ceases or the pulse drops to 0 V, the diaphragm 24 springs back into position, decreasing the chest cavity and expelling air out.

As shown in FIG. 2, the system 20 includes electrodes for stimulating the various muscles 28 and nerves 22. There are various types of electrode as set forth below in Table 1. The table discloses the various types of electrodes that may be used and advantages associated with each.

TABLE 1

Types of Electrodes and Advantages thereof

| TYPE OF ELECTRODE | ADVANTAGES |
|---|---|
| Surface | Metal plate with electrolyte gel, noninvasive |
| In/On Muscle | Lower thresholds and better selectivity compared to surface electrodes |
| Intramuscular | Implanted in the muscle, multistranded Teflon coated stainless steel wire, monopolar and bipolar configurations, good tensile strength, and flexibility |
| Epimysial | Implanted under the skin: on the muscle, monopolar and bipolar configurations, less prone to mechanical failure |
| BIONs | Injected into or near the muscle, hermetically sealed glass/ceramic capsule integrated with electronics |
| Near/On Nerve | Lower threshold levels and better selectivity than the above mentioned electrodes |
| Nerve Cuffs | Monopolar, bipolar and tripolar configurations, good power efficiency, improved selectivity, comparatively stable (for nerve stem only) |
| FINE | Reshape or maintain nerve geometry (for nerve stem only) |
| Intrafascicular | Penetrate the epineurium and into the fascicle, selective stimulation, lower current and charge levels (for nerve stimulation only) |
| LIFE | Stable, suitable for stimulating and recording |

In another embodiment, system 20 may comprise a micro or nanodevice implementation of the stimulus controller 100, wherein the stimulus controller 100 is implanted within the body of the user 21. In this exemplary system, the electrodes and sensors may communicate through wired lines or may communicate wirelessly with the stimulus controller 100. Similarly, one or more communication channels may couple to the stimulus controller 100 and the diaphragm 24 or phrenic nerve 22 for carrying signals there between. These one or more communication channels can be implemented using a variety of wired or wireless communication means including but not limited to wire or cable, fiber optics, conventional phone line, cellular phone link, wireless data communication link, RF link (such as Bluetooth™), or infrared link. In operation, the controller 100 may send an activation signal to the diaphragm 24 directly or the phrenic nerve 22, which sends a signal to the diaphragm 24. This activation signal may instruct the diaphragm 24 to contract or to drop down. When the diaphragm 24 contracts, the chest cavity increases and the lungs expand to fill with air. When the activation signal ceases or the pulse drops to 0 V, the diaphragm 24 springs back into position, decreasing the chest cavity and expelling air out.

Accordingly, the adaptive system 20 can account for muscle fatigue of the diaphragm 24 or lung compliance changes, as well as changing metabolic demands of the heart. As such, this adaptive system 20 provides personalized automatic physiological parameter settings for the user 21. The adaptive closed loop controller 100 may allow automatic fitting of electrical stimulation pulse parameters and can be used for long durations to account for muscle fatigue. Thus, this adaptive system 20 serves as a very useful product for providing respiratory therapy, especially to wean patients off of a mechanical ventilator. The customization of the adaptive system 20 achieves controlled pacing of pulse parameters, including breath-by-breath control of frequency and amplitude profile, using various outcome measures (e.g. lung volume, arterial, and/or expiratory carbon-dioxide ($CO_2$) levels).

Figure 3:
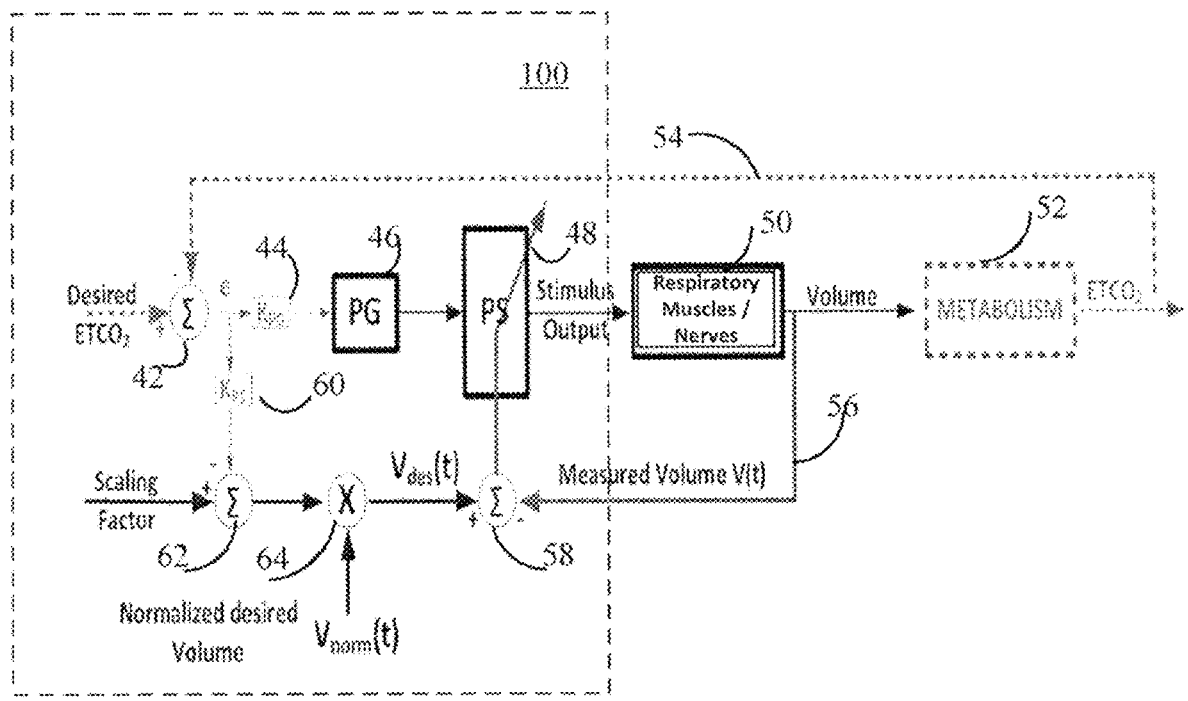
FIG. 3 shows a block diagram of a first example of a stimulus controller 100 of the adaptive system for pacing of respiratory muscles and nerves using neuromuscular stimulation shown in FIG. 2.

FIG. 3 shows a block diagram of a first example of a stimulus controller 100 of the adaptive system 20 for pacing of respiratory muscles and nerves using neuromuscular stimulation shown in FIG. 2. As shown, the stimulus controller 100 may comprise an adaptive feed-forward Pattern Generator/Pattern Shaper (PG/PS) assembly (46, 48) within a closed loop implementation, to control respiratory muscle movement using electrical stimulation after incomplete or complete paraplegia in human and animal models (including but not limited to rodents). This adaptive closed-loop ventilatory controller 100 can automatically customize and continually update stimulation parameters to achieve a desired breathing pattern with a fixed frequency and movement amplitude. In particular, the PG/PS assembly (46, 48) may provide an appropriate and customized stimulation of the respiratory muscles 50, including but not limited to inspiratory muscles (diaphragm, external intercostal) and expiratory muscles (internal intercostals and abdominal muscles) for natural and efficient breathing support to obtain a desired breath volume.

The PG/PS assembly (46, 48) within controller 100 may automatically customize the stimulation current pulse amplitude sent to each electrode, based on the error (e) between desired and measured physiological parameters of the user 21. The controller 100 may include a feed-forward loop section, and at least one feedback loop section. The feedback loop section may include the signal sent using line 54 relaying any number of physiological parameters related to respiration of the user, wherein the signal may be sent through a comparator 42 to be compared with a desired physiological parameter, including but not limited to $ETCO_2$, blood pH, lung volume, and oxygen levels. The error e between the desired and measured physiological parameters may be sent to a gain factor module 44 having a gain of $K_{PG}$. The scaled result may be sent to the pattern generator 46, which may generate a signal having an associated breathing pattern frequency. In response to the receipt of this breathing pattern frequency, the pattern shaper 48 may generate at least one associated amplitude and frequency of at least one stimulus control signal to be sent to a respiratory tissue 50, whether muscle or nerve. In an embodiment, feedback path 54 may represent a set-point feedback path, where the $ETCO_2$ level may be measured and subtracted from a constant $ETCO_2$ (set-point). The error e may be scaled by scaling factor $K_{PG}$ to provide a tonic drive to the pattern generator 46. This tonic drive can change the overall frequency generated by the pattern generator 46. Although not shown, the error signal could also change the network architecture of the pattern generator 46 by changing the connection weights between the neurons (described further with reference to FIG. 5), making the pattern generator 46 adaptive. This feedback signal 54 may also be used as control information for a module, which generates a desired normalized lung volume control signal; wherein, the signal is sent through a gain factor module $K_{PS}$, comparator 62, and multiplier 64. Additionally, the controller 100 may include another feedback loop section that includes a signal sent using line 56, which relays the measured lung volume to a comparator 58. The pattern shaper 48, which is also in the feed-forward path, can be adapted by the feedback signal 56; wherein, the architecture of the neural network of the pattern shaper 48 can be changed by changing the weights $W_1$, $W_2$, $W_3$ etc. (to be described in more detail with reference to FIG. 5). In particular, the pattern shaper 48 may be adapted based upon the error between a cyclic desired lung volume and the cyclic instantaneous lung volume measured during each breath. That is, the error between the desired normalized lung volume and the measured lung volume may be used to provide a control signal to the pattern shaper 48, which generates a stimulus control signal to the respiratory muscles and/or nerves 50, resulting in an adjustment to the lung volume.

In another embodiment (not shown), the desired cyclic lung volume can also be changed based on the error between the detected and desired $ETCO_2$ level. Further, in an additional embodiment (not shown), the error between the desired and measured lung volumes can directly control the stimulation to the respiratory muscles in a third feed-back loop.

Further, in yet another embodiment (not shown), the architecture of the pattern generator 46 can be adapted based on the error between a cyclic desired lung volume and the cyclic instantaneous lung volume measured during each breath. In this embodiment, the pattern generator 46 can generate a fixed breathing pattern frequency, while the feedback path 54 may be eliminated.

In many embodiments, the stimulus controller 100 may comprise a pattern generator 46 coupled to a pattern shaper 48, wherein the pattern shaper 48 provides a stimulus signal to one or more electrodes 28 (as shown in FIG. 2) coupled to one or more respiratory muscles 50. After the time necessary for metabolism, a sensor 30 may, for example, detect the $ETCO_2$ level of the exhaled breath of the user. This detected $ETCO_2$ level may be sent to the comparator 42 as feedback control information as described above. The comparator 42 may compare a desired $ETCO_2$ level with the detected $ETCO_2$ level and generate the error (e) between the two. This error (e) may be amplified by gain factor module $K_{PG}$ and fed as input into pattern generator 46. The role of the pattern generator 46 may be to provide general timing information for producing a given cyclic breathing pattern (i.e., it provides an oscillatory signal at the desired movement frequency). The output signal of pattern generator 46 may be adaptively customized by the pattern shaper 48 to determine the specific stimulation pattern used to activate the muscle 50. The breathing pattern frequency as defined by pattern generator 46 can be altered in real time using the feedback 54 supplied from sensors 30, which detect certain physiological statistics, such as the $ETCO_2$ of the user (as shown in FIG. 2). The stimulation of the nerve and/or muscles as generated by the pattern shaper 48 may occur at a higher frequency than the breathing pattern frequency, which is generated by the pattern generator 46. The pattern shaper 48 may use pattern recognition to recognize patterns and regularities in data through the use of a learning algorithm (to be explained in detail with respect to FIG. 5). Further, pattern shaper 48 may set the pulse width, the inter-pulse interval (time between each stimulus pulse), the charge balance, and/or the inter-pulse gap (or delay) between the negative and positive phases of each stimulus pulse. Accordingly, the pattern shaper 48 may set the cyclic pattern equal to the breathing pattern frequency (slow), while the muscle or nerve may be stimulated at a higher frequency in order to achieve contraction of this muscle. The pattern shaper 48 may generate the stimulus control signal sent to the electrodes implanted within the muscles and/or nerves for controlling the breathing pattern of the patient, where the stimulus control signal may include the frequency, amplitude, the pulse width, the inter-pulse interval (time between each stimulus pulse), the charge balance, and/or the inter-pulse gap (or delay) between the negative and positive phases of each stimulus pulse.

Figure 4:
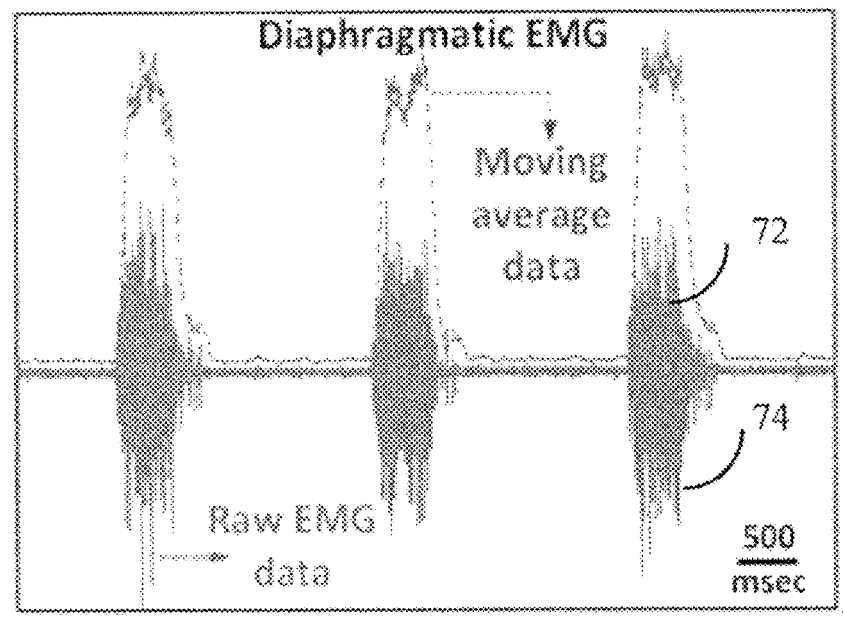
FIG. 4 shows a diagram of a diaphragmatic Electromyogram (EMG) of a normal breathing pattern of a healthy person, including but not limited to a human being or an animal.

FIG. 4 shows a diagram of a diaphragmatic EMG of a normal breathing pattern of a healthy person, including but not limited to a human being or an animal. FIG. 4 is presented for illustrative purposes and not to represent the breathing pattern of a person that has sustained a SCI. Rather, it illustrates an ideal model of a breathing pattern frequency and associated alert signals generated by the brain to stimulate the respiratory tissue (this ideal model is compared and contrasted with the model of the adaptive system 20 disclosed herein below). In particular, when a person breathes in normally, the person's breathing pattern 72 possesses a specific frequency and volume. Each breath will have an inspiratory duration and an expiratory duration. During the inspiratory portion of the actual breathing pattern 72, multiple muscle fibers are recruited at a high frequency and their electrical activity is summated, and then the recruitment falls close to zero during the expiratory portion, as illustrated. Under normal functioning, when a person's $CO_2$ levels rise above a certain threshold, the brain sends an alert signal 74 (at approximately 20-25 Hz) to the phrenic nerve, commanding it to breathe faster and/or deeper. Similarly, when the brain senses a change in metabolic levels, blood pH levels, and/or blood oxygen levels, the brain may generate an alert signal 74, which is sent to the phrenic nerve to increase the breathing pattern. As shown, the frequency and amplitude of the alert signal 74 sent by the brain to trigger movement in any of the respiratory muscles is generally faster in frequency than that of the breathing pattern 72, where the breathing pattern 72 provides an envelope for the alert signal. That is, the alert signal 74 mimics the shape of the breathing pattern 72 during the inspiratory portion; yet, it has a faster frequency. In particular, the alert signal 74 for the respiratory muscle shown relates to the diaphragm, but it does not have to be limited to the diaphragm. When the signal 74 is sent to the phrenic nerve, the diaphragm contracts and the chest cavity increases, causing the lungs to expand and fill with air. When the signal from the phrenic nerve ceases, the diaphragm springs back into position, decreasing the chest cavity and expelling air out of the lungs.

Referring back to the operation of controller 100 in FIGS. 2 and 3, controller 100 may stimulate any particular respiratory muscle of the user 21 having an SCI. In the case where it stimulates the diaphragm, controller 100 may stimulate the diaphragm 24 at a particular rate of speed, monitoring how many breaths per minute the user may need. The pattern generator may generate the breathing pattern frequency at a low rate, similar to the actual breathing pattern 72 shown in FIG. 3. In response to the breathing pattern frequency generated by the pattern generator 46, the pattern shaper 48 of FIG. 3 may generate the amplitude and frequency of the stimulus pulse to be sent to stimulate and contract at least one tissue 50, whether muscle or nerve. The frequency of the stimulus pulse can be at a higher frequency similar to alert frequency 74 that naturally occurs as shown in FIG. 3. Thereby, the stimulus controller 100 may respond to changes in the physiological parameters by adjusting the breathing pattern to conform to a desired set of physiological parameters, including but not limited to end tidal $CO_2$, blood pH, lung volume, and oxygen levels.

More particularly, the pattern generator (PG) 46 may produce a cyclic pattern having the frequency of the breathing pattern of the person or animal coupled to the controller 100. The pattern generator 46 may determine the breathing rate (rhythm) of the individual through the use of an artificial neural network. Artificial neural networks are generally presented as systems of interconnected "neurons" which can compute values from inputs, and are capable of machine learning as well as pattern recognition due to their adaptive nature. The pattern generator 46 may possess the capacity to respond slowly to physiological changes, such as metabolic demand of the body as indicated by the sensed physiological parameters detected by the various sensors (30, 32). Simultaneously, pattern generator 46 may change the overall respiratory rate of the user, as well as quickly respond to external perturbations, such as volatile irritants. In addition, the pattern generator 46 may change the frequency or reset the rhythm by terminating an inhalation and restarting the entire breathing pattern.

Figure 5:
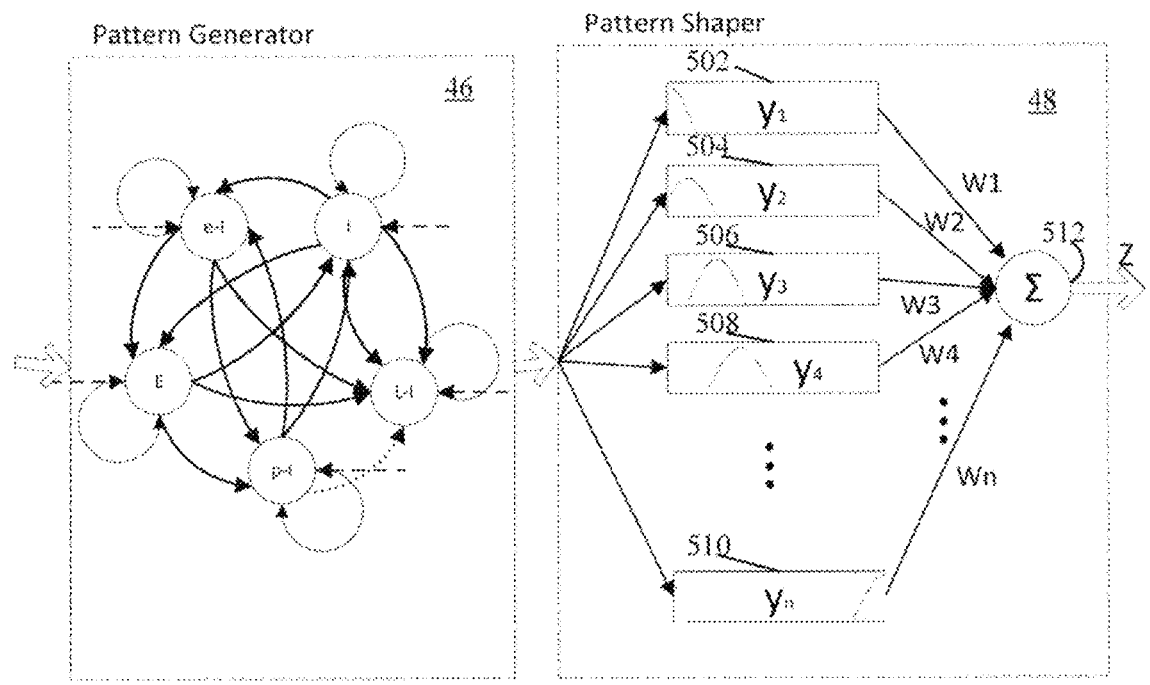
FIG. 5 illustrates a block diagram of pattern generator 46 and pattern shaper 48 of FIG. 4.

FIG. 5 illustrates a block diagram of pattern generator 46 and pattern shaper 48 of FIG. 4. Referring to FIG. 5, the pattern generator 46 may comprise a neuromorphic non-linear oscillator made of a network of neurons. In such a neuromorphic non-linear oscillator, the overall frequency of the network can be changed by driving the neurons with a tonic input. Initially, the pattern generator 46 can be set to a fixed frequency (rate) of breathing. The frequency can be calculated using the Otis equation that utilizes a person's weight. In the alternative, the pattern generator 46 may change its frequency based on one or more physiological parameters. Notably, the feedback 54 sensed by a sensor (coupled to line 23 of FIG. 2) may be used to change the tonic drive of the pattern generator 46 as a function of the physiological state of the person as shown in FIGS. 2 and 4. For example, the end-tidal $CO_2$ or arterial $CO_2$ or oxygen levels may be used to proportionally change the tonic drive. Further, in another embodiment, another sensor could be used to sense the chemical composition of the exhaled breath, wherein the chemical composition is used as feedback control information for adjusting the breathing pattern frequency. In the alternative, the continuous measure of the oxygen levels in the blood may be obtained using optical sensors, wherein the oxygen level is used as feedback control information for adjusting the breathing pattern. Moreover, the pattern generator 46 may also be entrained to a different external cyclic frequency not dependent upon the user's physiological state.

The neural network structure of the pattern generator 46 may be based upon a 5-neural network mimicking the simplified connectivity pattern of brain stem neurons in mammals to produce rhythmic breathing pattern output. In one example, the five types of neurons for breathing rhythm, representing the five respiratory neuronal groups, include: inspiratory, late-inspiratory, post-inspiratory, expiratory, and early-inspiratory neurons. In particular, different groups of neurons with firing patterns related to the respiratory rhythm have been identified in the brainstem clustered mainly in two areas of the medulla: the dorsal respiratory group (DRG) and the ventral respiratory group (VRG). These neurons are classified as inspiratory (I), post-inspiratory (p-I) and expiratory (E) neurons according to the respiratory phase at which they are active. The inspiratory neurons may further be classified into early inspiratory (e-I), ramp inspiratory (I), and late inspiratory (L-I) neurons. Late inspiratory neurons may be referred to as off-switch (OS) neurons. The model implemented for the pattern generator 46 may be implemented using these five different respiratory related neuronal groups. The connections between these groups as shown in FIG. 5 may be based upon experimental results using various anatomical and electrophysiological techniques.

The number of neurons used to form a network can be modified to fewer neurons or the 5-neural network may be replaced by a single neuron that has pacemaker properties. Each neuron provides a periodic output signal that can be utilized to provide the periodic drive signal to the pattern shaper 48. All neurons of the pattern generator 46 are driven by a constant tonic input (as indicated by the dashed arrow feeding each neuron) and a self-excitation input (indicated by the arrow looping back on itself on each neuron). The tonic inputs represent chemoreceptor drives, in particular, and likely also represent inputs from supramedullary (e.g., pons, hypothalamus) and other medullary (e.g., reticular activating system) mechanisms. Further, one or more neurons of the pattern generator 46 could be driven by a phasic input, obtained from signal data capturing from the sensors 30 and 32 during ventilation.

In one model (incorporated by reference herein; Botros, et. al., "Neural Network Implementation of a Three-Phase Model of Respiratory Rhythm Generation," Biological Cybernetics (1990)), the I group receives inhibitory inputs from the E, p-I and L-I groups. The inhibitory inputs from the E and p-I neurons may be based on intracellular recordings from I neurons showing the presence of Inhibitory PostSynaptic Potential (IPSP) during the post-inspiratory and expiratory phases. Additionally, expiratory neurons of the Bötzinger complex send inhibitory connections to areas of the Ventral Respiratory Group (VRG) and Dorsal Respiratory Group (DRG) which have large populations of I neurons. The inhibition from L-I neurons is based on the observation that the firing of the L-I neurons coincides with the inhibition of the I neurons at the end of the I phase. The E group receives inhibitory inputs from the I and e-I groups. These inhibitory connections are based on intracellular recordings from E neurons which reveal IPSPs during the I phase. The pattern of synaptic inhibition observed in some E neurons to be similar to the pattern of activity of I neurons, while in other E neurons it was similar to the pattern of activity of e-I neurons. Further, I neurons in the VRG and DRG send inhibitory connections to some E neurons. Similarly e-I neurons appear to project to the contralateral E neurons. The post-inspiratory group receives inhibitory connections from E and e-I groups, while the e-I group receives inhibitory inputs from the I and p-I groups. Anatomical studies have shown that e-I neurons may receive collaterals from neurons in the DRG and the Bötzinger complex. The decay of activity of e-I neurons may mirror the increasing activity of the I neurons. Moreover, the time course of the declining inspiratory inhibition during expiration may connote that early-peak expiratory activity inhibits the "on-switch" of inspiration, which is attributed to e-I neurons in this model. This declining inhibition may be due to p-I neurons or to other early-expiratory neurons which are not distinguished from p-I neurons in the present model.

The L-I group receives an excitatory input from the I group and inhibitory inputs from the e-I and E groups. Inhibition from the e-I and E groups may occur due to the pattern of inhibition of L-I neurons during the inspiratory and the expiratory phases matches the patterns of activity of the e-I and E groups respectively. Furthermore, e-I neurons respond oppositely to L-I neurons during lung inflation.

The dynamic behavior of each neuron pool may be modelled such that each group of neurons may be considered as a single unit, receiving common inputs and having the same output. The output of each group may represent the average potential of the neurons in the group. The synaptic weights between the groups may represent the average synaptic connectivity. The rate of change of the activity of one neural group may be equal to a weighted sum of: (i) the activities of the other groups (each transformed by a sigmoidal function), (ii) a tonic input, (iii) a positive self-feedback, and (iv) a decay term proportional to the output of the group. There are various ways in which the dynamic activity of each neuron of the neural network within the pattern generator 46 may be modeled. One implementation may be that which was described in U.S. Pat. No. 8,790,282, which is incorporated by reference herein. Another such dynamic activity of each neuron may be described using the following differential equations:

where:

$$\frac{dX_i}{dt} = 1a_i \cdot X_i = \sum_{j=1, \neq i}^{5} W_{ji} \cdot S(X_j) + W_{ij} \cdot S(X_i) + B_i$$

$X_i$ represents the output of one of the 5 neuronal groups—i.e., I (inspiratory), E (expiratory), post-inspiratory (p-I), early inspiratory (e-I), ramp inspiratory (I), and late inspiratory (L-I).

$W_{ji}$ is the coupling parameter from the j-th group to the i-th group, $\alpha_i$ is a measure of the rate of decay of the activity of the i-th group if no input is present, $B_i$ represents the tonic input to the i-th group. This input includes physical inputs from different neural structures, as mentioned previously, and may also represent relative differences in excitability between the different groups, $S(\bullet)$ is a sigmoidal function relating the frequency of firing of one group to its activity. This function is of the form:

$$S(X) = K \cdot \alpha + (1 - K) \cdot \beta$$

$$\alpha(X) = \{\min(X, 4) X \geq 0; 0 X < 0$$

$$\beta(X) = \frac{4}{1 + e^{-1.75 \cdot (X-2)}}$$

where K is a constant with a value between zero and one which determines the degree of "smoothness" of S(X). In the present embodiment, K may be equal to 0.6.

The sigmoidal function relating the firing frequency of one group to its activity can also be implemented as a nonlinear function given by a seventh order polynomial h(X) with a strict threshold and saturation that has been appropriately scaled. Such an embodiment is better suited for a hardware implementation.

Combining the mathematical representation of each neural group with the proposed connections between the different respiratory groups (FIG. 1) results in the following system of ordinary nonlinear differential equations (Eq. set 1):

$$\frac{dI}{dt} = -a_I \cdot I - W_{EI} \cdot S(E) - W_{PI} \cdot S(P) - W_{LI} \cdot S(L) + W_{II} \cdot S(I) + B_I$$

$$\frac{dL}{dt} = -a_L \cdot L + W_{IL} \cdot S(I) - W_{EL} \cdot S(E) - W_{RL} \cdot S(R) + W_{LL} \cdot S(L) + B_L$$

$$\frac{dP}{dt} = -a_P \cdot P - W_{EP} \cdot S(E) - W_{RP} \cdot S(R) - W_{PP} \cdot S(P) + B_P$$

$$\frac{dE}{dt} = -a_E \cdot E - W_{IE} \cdot S(I) - W_{RE} \cdot S(R) - W_{EE} \cdot S(E) + B_E$$

$$\frac{dR}{dt} = -a_R \cdot R - W_{IR} \cdot S(I) - W_{PR} \cdot S(P) - W_{RR} \cdot S(R) + B_R$$

where P, R, and L represent p-I, e-I, and L-I neurons respectively.

With these membrane properties and the interconnections, under appropriate constant tonic drive the preferred embodiment of the pattern generator 46 of the present application generates a stable oscillation over a range of frequencies spanning normal breathing for all ages, for example approximately 0.15 Hz to 1 Hz; and possesses neurons that receive tonic drive current, synaptic current from other PG neurons and could also receive external current from sensors 30, 32, and 36 derived signals. The cyclic output from the pattern generator 46 provides feedforward input to the pattern shaper 48.

Similarly, the pattern shaper 48 may comprise a single layer neural network to determine over the course of time the amplitude and frequency of each stimulus pulses used to stimulate the muscle and/or nerve. In particular, the pattern shaper 48 may function by generating a consistent pattern of several time-shifted raised cosine waves and then combining them to determine the stimulation to the muscle/nerve. The pattern shaper 48 may scale the contribution of each basis function to determine the parameters for the stimulation values. This process of scaling may rely upon a learning algorithm that utilizes the error (e) between a desired breath/lung volume and the actual breath/lung volume for the current time and prior time steps. Thereby, pattern shaper 48 can adjust the stimulation current amplitude automatically such that the desired breath-to-breath shape of the lung volume displacement trajectory may be obtained.

It should be understood that the pattern generator 46 and pattern shaper 48 neurons can be implemented in either software or in hardware embodiments. Software implementation can be supported in a computer or a computer-readable medium.

In many embodiments, the pattern generator 46 can work as an autonomous oscillator, meaning that it does not need periodic drive signal input from the sensors 30, 32, or 36 to enable oscillation. Additionally, the system's speed of operation can be entrained to an external signal input from the sensors 30, 32, or 36 to the pattern generator 46. Additionally, the programming of if-then rules are not required to adjust the pattern generator 46 signal output. The pattern generator 46 could also be programmed to respond to simultaneous inputs from more than one entrainment, and thus can be entrained and respond to brief changes in physiological parameters at the same time.

The pattern generator 46 may have the ability to be entrained at a variety of frequencies that would be within the range of human and animal breathing patterns. Current in proportion to the amplitude of a simulated phasic input may be provided, while the pattern generator 46 oscillation frequency is monitored. In a particular embodiment, under default conditions, the pattern generator 46 oscillates at a pre-entrainment default frequency ($f_{pre}$). Once entrainment begins, the pattern generator circuit 46 quickly assumes the frequency ($f_{post}$) of the current input. The pattern generator circuit 46 can thus be entrained to a 1:1 ratio ($f_{post}/f_{pre}$) For example, the pattern generator circuit 46 produces an oscillatory signal in response to sensor input, which signal follows the frequency of the breathing pattern. The frequency of the pattern generator can also be changed by increasing or decreasing the tonic drive to the neurons. This frequency could range from 0.1 Hz to 1 Hz easily encompassing the range of breathing frequency of adults.

An implantable pulse generator 46 connected to the electrodes implanted in muscles near the neuromuscular junction or in the nerves or in combination could be wirelessly controlled by an external unit that consists of a custom PG/PS controller. The external unit could be made on a field-programmable gate array (FPGA) or other custom chip and could be used to transmit the stimulation pulse parameters. The electrodes in the diaphragm and/or intercostal muscles could be installed using a laparoscopic approach.

In operation, the system 20 stimulates the diaphragm at a particular rate of speed, monitoring how many breaths per minute the user may need. Each breath will have an inspiratory duration and an expiratory duration. The difference between actual volume and desired breath volume may be used as feedback to change the breathing pattern. The pattern shaper 48 comprises a learning algorithm that detects a difference in the breathing pattern and sends a corresponding signal to adjust the detected breathing pattern. In one example, when a difference occurs between the actual $ETCO_2$ and the desired $ETCO_2$, the difference will be supplied by summer 42 to a gain factor ($Kp_G$), which may be either linear or non-linear gain. This difference may occur when the level of $CO_2$ accumulates if, for example, the user may be breathing at a pace that is too shallow to expel the $CO_2$ at the desired rate and level. This difference represents the error between the actual and the desired level of $CO_2$. That is, the difference represents the error in how deeply the user breathes. The gain factor module $K_{PG}$ output may be fed into the pattern generator 46, which is continuously oscillating, and thereby, providing a frequency of oscillation for the breathing pattern. The gain factor module $K_{PG}$ enables a change in the drive supplied to the pattern generator 46. This change in drive may change the frequency of oscillation. In the initial stages of operation, the frequency of the pattern generator 46 may be tuned. The pattern generator 46 adjusts the frequency to a certain number of breaths a minute, effectively setting the pace of the breathing. The pattern shaper 48 comprises another set of neurons that decide what stimulation should be given to the muscles and/or nerves. Output from the pattern shaper 48 can be a command that instructs the electrode to send a pulse at a greater amplitude. The controller 100 may include is a gain factor ($K_{PS}$) for the pattern shaper 48. The scaling factor and the pattern shaper gain factor $K_{PS}$ may be summed together and multiplied by a normalized volume $V_{norm}(t)$ at multiplier 58 to generate a desired volume $V_{des}(t)$. This desired volume $V_{des}(t)$ may be compared with the measured volume V(t) at summer 56. The result will determine how the pattern shaper adjusts the output stimulus.

In certain embodiments, the neural networks of the pattern generator 46 and the pattern shaper 48 can be implemented in software. Further, the adaptive system 20 may comprise a software implementation based on statistics and signal processing in lieu of the neural networks. This type of statistical modeling system may use probability and mathematical functions to determine the most likely pattern match. One model may comprise the Hidden Markov Model, which involves complex mathematical functions, which take the information known to the system to figure out hidden information. Similar to the neural network model, in an effort to distinguish between all the possible breathing patterns and volumes, this statistical system may require exemplary training data to reach their optimal performance. As discussed herein, another embodiment may comprise a nanodevice implementation of the PG/PS assembly (46, 48) controller system, having the capability for very large scale principal components. This implementation may be implanted within the user and controlled wirelessly.

The proposed innovative respiratory pacing system 20 will enable improved respiratory management by personalizing stimulation parameters for the individual. The system can automatically personalize stimulation parameters to account for the non-linear properties of muscle activation and muscle fatigue. This system 20 can also adjust to meet changes in the metabolic demands of the user and decrease the rate of muscle fatigue by producing efficient ventilation. Because of the adaptive nature of stimulation, the system 20 could be used in an intermittent pattern as ventilatory assist for those with some degree of ventilatory control and provide long-duration pacing with reduced muscle fatigue.

The proposed system 20 could be used long-term (e.g., years) for respiratory assistance by people with complete paralysis of the respiratory muscles or in the short term (e.g., weeks) for respiratory therapy by people with impaired control of the muscles as after incomplete SCI or diseases such as COPD.

Overall, the system 20 may provide improved quality of life for the user and simplified deployment for the clinician and caregiver. Another feature of the system 20 is that it produces an oscillatory rhythm and coordinates a set of actuators on short timescales to control complex processes with dynamics over much longer timescales. The proposed neuromorphic control strategies could be useful for other challenges such as the control of cyclic movements, the control of brain stimulation to avoid epileptic seizures or minimize symptoms in Parkinson's disease, the control of metabolic processes, or drug dose scheduling.

Further, as shown in FIG. 5, the pattern shaper 48 may be a single-layer neural network where each neuron's output may be in the shape of a raised cosine waveform, thus forming a set of basis functions. As shown, pattern shaper 48 may comprise a learning algorithm including n basis functions ($Y_1, Y_2, Y_3, Y_4 \ldots Y_n$) (502, 504, 506, 508, 510). Each neuron's output, represented by $Y_j(t)$, may possess the shape of a raised cosine waveform. The set of input neurons are activated by the output from pattern generator 46. After being weighted using weight functions ($W_1, W_2, W_3, W_4, \ldots W_n$) and transformed by a function 512 (e.g., a function determined by the network's designer), the activation of these input neurons can then be passed on to other neurons. This process is repeated until finally, an output neuron is activated. The number of basis functions (neurons in the neural network) may be set, e.g., to be equal to the number of time steps across a desired breathing period, where the basis function outputs are time-shifted with respect to each other as shown. The network parameter $\eta a$ determines the width of each individual basis function, where each basis function may be set to have activity spread (nonzero values) over $\eta a$ time steps. The controller output of the pattern shaper 48 at each time step, denoted by z(t), is a weighted summation of the basis functions.

$$z(t) = \sum_{j=1}^{m} w_j(t) y_j(t)$$

where $y_j(t)$ is the output of the basis function j at time t, m is the number of basis functions, and $w_j(t)$ is the output weight for basis function j. The network output value z(t), which has an output range from 0 to 1, is scaled by the maximum stimulation intensity (stimulus current amplitude) for each channel.

The pattern shaper 48 modifies the output weights $w_j(t)$ in order to scale the contribution of each basis function to the pattern shaper 48 output time series. Given the inherent delays between muscle stimulation and breathing, an error in breathing pattern at a given time can be attributed to the errors in past stimulation values. Therefore, the pattern shaper learning algorithm uses the error at the current time step to change the weights on basis functions that were active at prior time steps.

$$\Delta w_j(t) = \eta e(t) \sum_{k=1}^{n} \frac{1}{n} y_j(t - kT)$$

where $\Delta w_j(t)$ is the change in output j of the pattern shaper network, η is a constant learning rate, e(t) is the error measured between the desired and measured angle, T is the controller update period, and n is the number of past activation values used by the algorithm. The constant learning rate η may be set 0.002 and n may be set to either 7 or 9. These are general settings that can be changed to allow faster or slower learning and adaptation of the pattern shaper.

Figure 6:
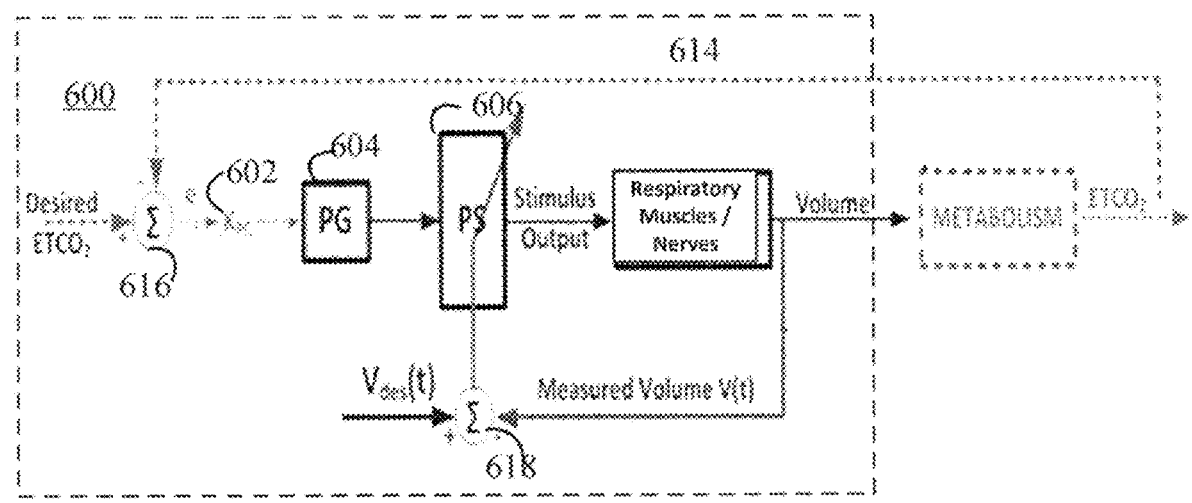
FIG. 6 shows a block diagram of a second example of a stimulus controller of the adaptive system for pacing of respiratory muscles and nerves using neuromuscular stimulation without feed-forward control that adapts the neural network of the pattern shaper 48.

FIG. 6 shows a block diagram of a second example of a stimulus controller 600 for pacing of respiratory muscles and nerves using neuromuscular stimulation without feedforward control that adapts the neural network of the pattern shaper 48. In this alternative embodiment, the desired breathing volume $V_{des}(t)$ may be directly input into the system as opposed to being generated from the gain factor corresponding to the difference between the actual and desired physiological parameter level as shown in FIG. 4. Accordingly, components of the controller 600, including comparators (616, 618), gain module 602, pattern generator 604, and pattern shaper 606, may function similar to the components of controller 100 as shown and described in FIGS. 3 and 5.

Figure 7:
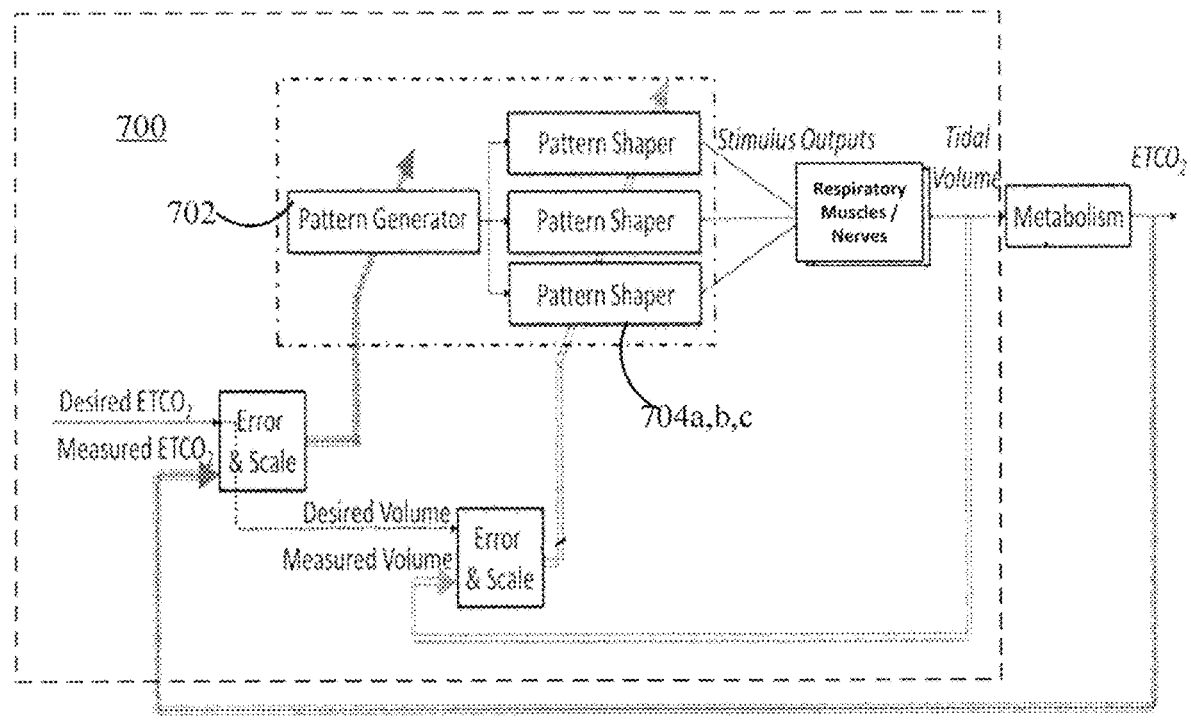
FIG. 7 illustrates a block diagram of a second example of an adaptive system for pacing of respiratory muscles and nerves using neuromuscular stimulation.

FIG. 7 illustrates a block diagram of a second example of an adaptive system for pacing of respiratory muscles and nerves using neuromuscular stimulation. As shown, a single pattern generator 702 drives multiple pattern shapers (704a, 704b, and 704c), with each pattern shaper adjusting the stimulation levels to a differing muscle or nerve. The pattern shaper (704a, 704b, and 704c) may control more than one muscle. Muscles of inspiration (and nerves innervating them) would contract (activate) out of phase with those for expiration. For example, the pattern shapers (704a, 704b, and 704c) may send stimulus to any of the extra-diaphragmatic respiratory muscles, including the external upper intercostals for inspiration and the abdominal muscles for expiration. The learning algorithm may be implemented where one of the pattern shapers (704a, 704b, or 704c) may be used to stimulate a respective one of the muscle groups. Accordingly, components of the controller 700, including pattern generator 702, and pattern shapers (704a, 704b, or 704c), may function similar to the components of controller 100 as shown and described in FIGS. 3 and 5.

Figure 8:
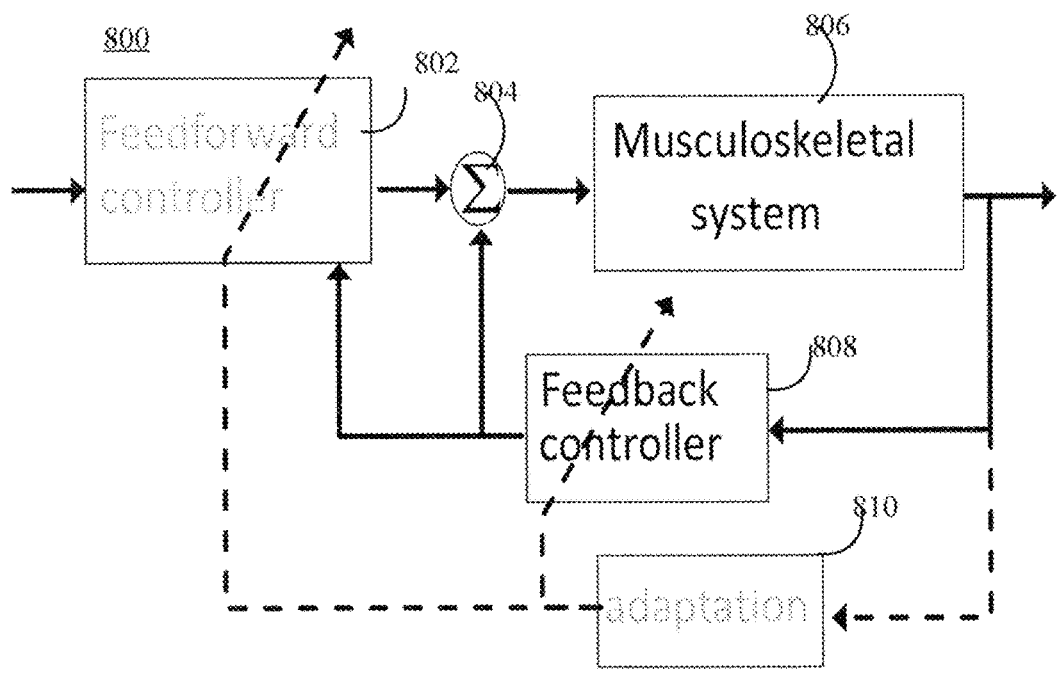
FIG. 8 illustrates a block diagram of a third example of an adaptive system for pacing of respiratory muscles and nerves using neuromuscular stimulation.

FIG. 8 illustrates a block diagram of a third example of an adaptive system 800 for pacing of respiratory muscles and nerves using neuromuscular stimulation. A feedforward controller 802, comprising a PG/PS assembly, sends a stimulus signal to a comparator 804, which compares the output of the feedback controller 808 to the output of the feedforward controller 802. The output of comparator 804 represents the difference between the two, which is sent to the musculo-skeletal system 806, comprising respiratory tissue of a human or animal. The output of feedback controller 808 may provide input to the feedforward controller 802 for providing real-time physiological parameters as input into the pattern generator and/or pattern shaper. The system may further comprise an adaptation module 810 that adapts the pattern generator and/or pattern shaper included within the feedforward controller 802 and/or the feedback controller 808.

Figure 9:
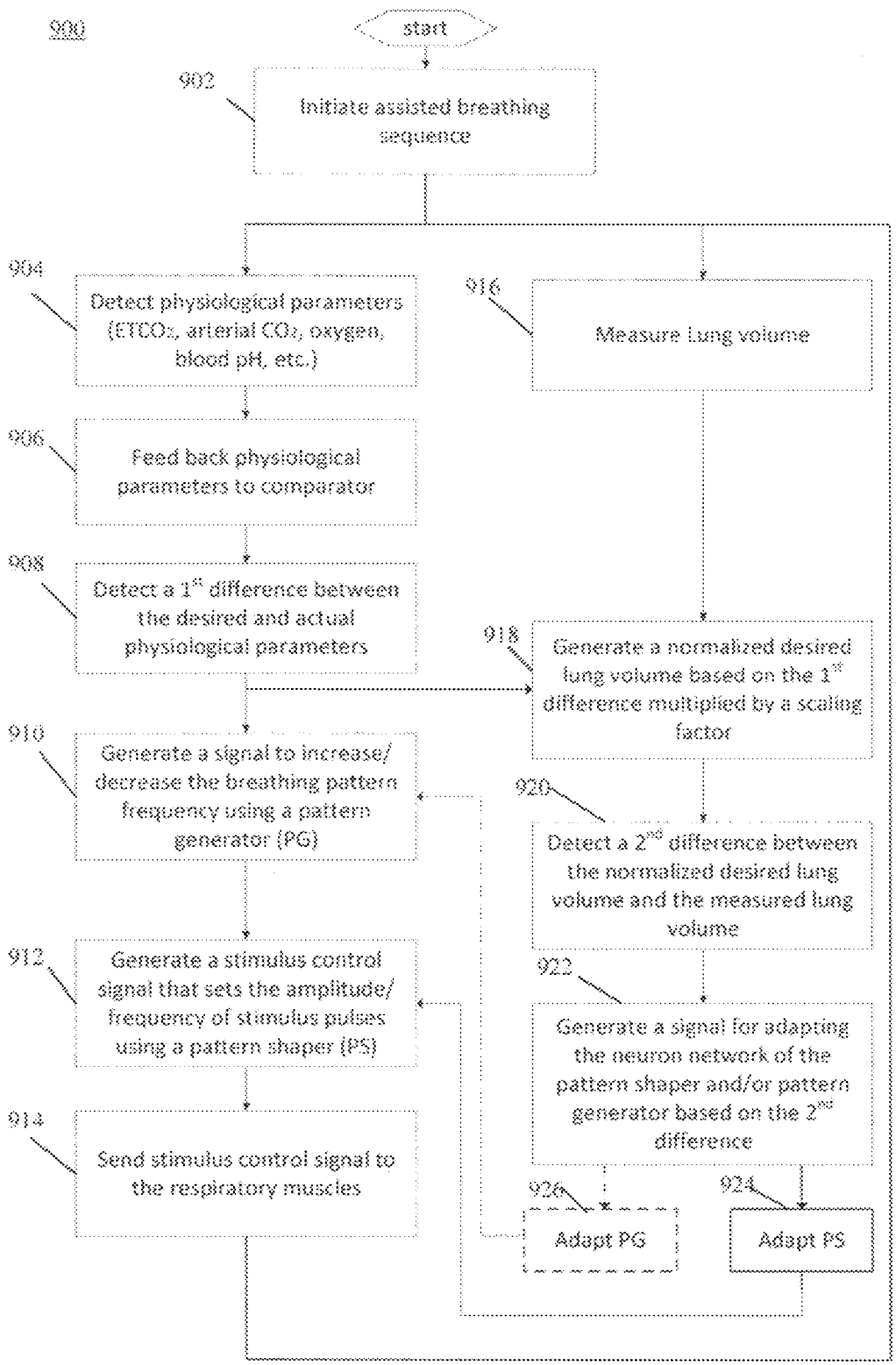
FIG. 9 illustrates a flow chart of an example process for a method of adaptively pacing respiratory muscles and nerves using neuromuscular stimulation.

FIG. 9 illustrates a flow chart of an example process 900 for the method of adaptively pacing respiratory muscles and nerves using neuromuscular stimulation. In a first step 902, a breathing sequence may be initiated by sending a pulse to one or more respiratory muscles. In two simultaneous steps (904 and 916), physiological parameters and the lung volume is measured, respectively. The physiological parameters may be fed forward to a comparator to compare a set of desired physiological parameters with the detected physiological parameters (step 906). The difference between the desired and detected physiological parameters may be calculated and a signal may be generated that increase and decrease the breathing pattern frequency using a pattern generator (in respective steps 908 and 910). Simultaneously, the difference between the desired and detected physiological parameters may be used to generate a desired normalized lung volume in step 918. The difference between the desired normalized lung volume and the measured lung volume can be detected at step 920. This difference may be used for adapting the neural network of the pattern shaper to increase/decrease the lung volume in steps 922 and 924. Optionally, the differences may be used for adapting the neural network of the pattern generator in steps 922 and 926. The pattern shaper may generate a stimulus control signal, including the frequency and amplitude of the stimulus pulse, for adjusting the breathing pattern to the desired normalized lung volume and the desired physiological parameters (step 912). Finally at step 914, the signal may be sent to the respiratory muscles and the process may be repeated starting at steps 904 and 916.

The advantages of the adaptive system for pacing of respiratory muscles and nerves using neuromorphic controlled neuromuscular stimulation include a design that stimulates both diaphragmatic/intercostal muscles or phrenic nerve and intercostal nerve or a combination of muscles and nerves. Further, the system disclosed herein may comprise a controller that automatically fits stimulation parameters to achieve the desired breathing pattern and, hence, is self-customized to the user. Additionally, the system can automatically adjust stimulation parameters to account for diaphragmatic fatigue and compromised lung compliance. Moreover, the system may automatically adjust the frequency of the breathing pattern based on metabolic demand or the change thereof. As the muscles become stronger or atrophy reduces, the examples of an adaptive system disclosed herein may automatically adjust the stimulation charge, including but not limited to the amplitude and/or pulse widths of the pulses. Finally, if the user can breathe partially on their own, the adaptive system may be used to stimulate the respiratory muscles/nerves to enhance the muscles contractions to achieve the desired volume, thus providing ventilatory assist; which is a beneficial option for providing rehabilitation therapy.

The methods and processes described herein can be embodied as code and/or data. The software code and data described herein can be stored on one or more computer readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals.

Experimental Results

Figure 10:
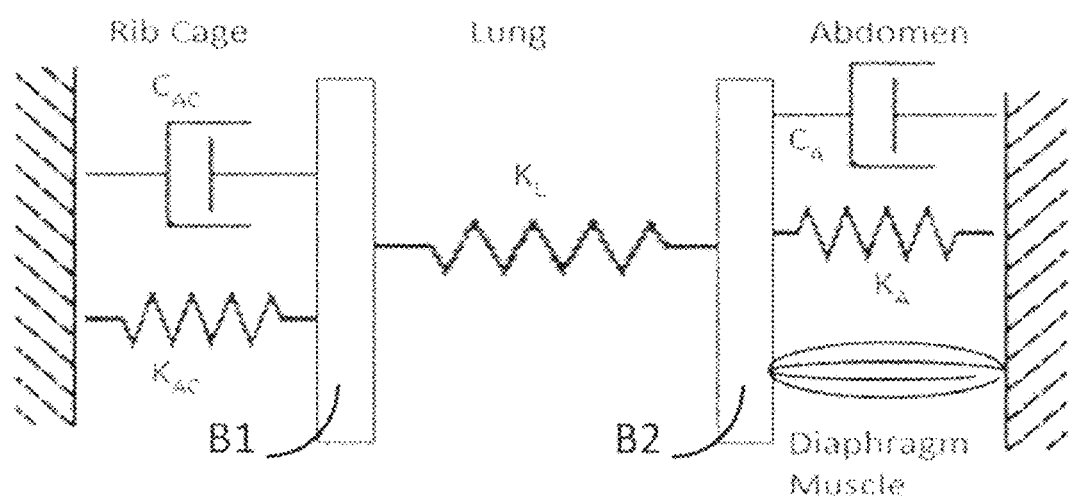
FIG. 10 illustrates a block diagram for an example of a computational diaphragm lung model for use with testing the adaptive respiratory system disclosed herein.
Figure 11:
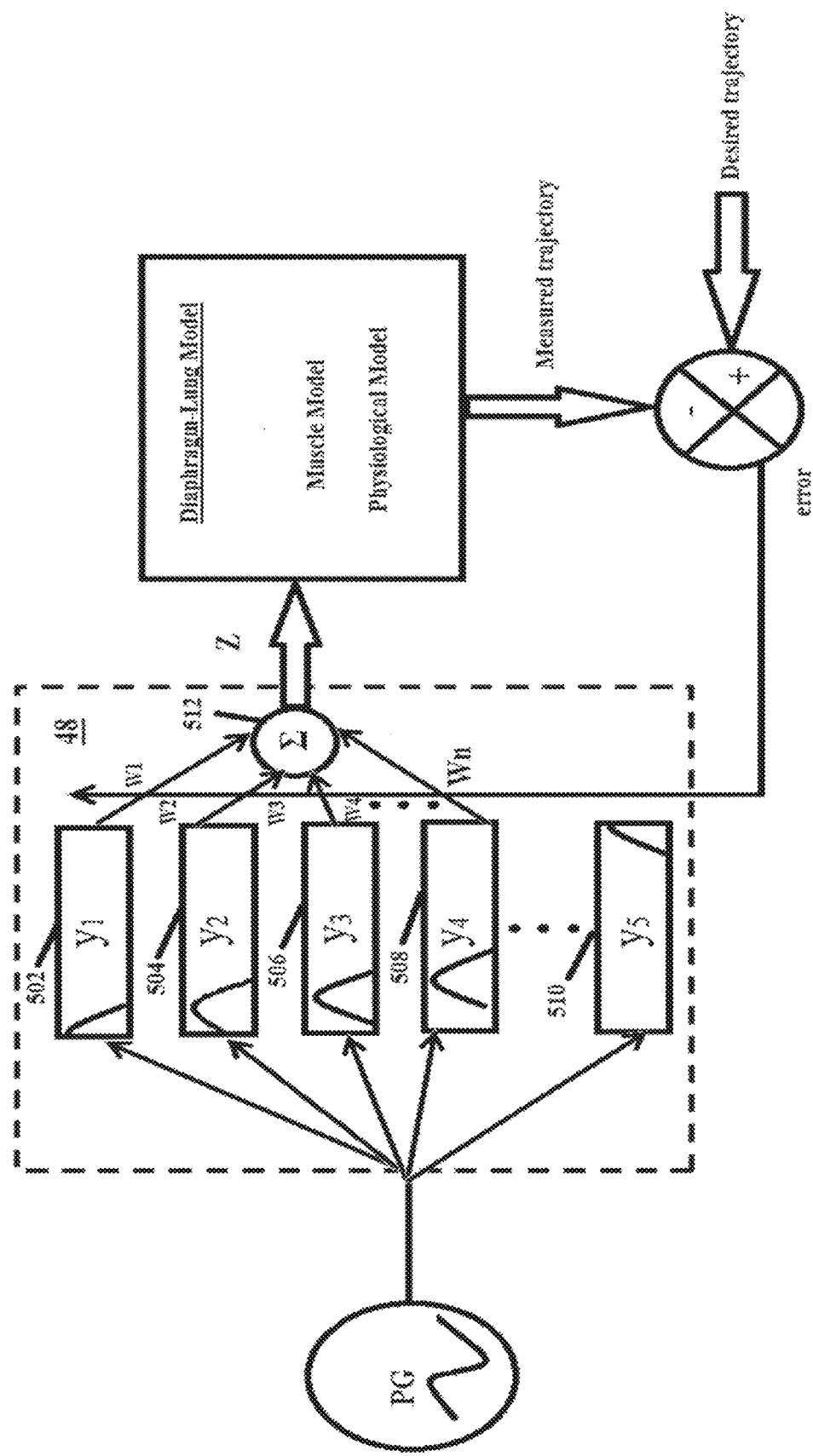
FIG. 11 displays a block diagram of diaphragm lung model of FIG. 10 coupled to the pattern generator/pattern shaper arrangement of FIG. 5.

FIG. 10 illustrates a block diagram for an example of a computational diaphragm lung model for use with testing the adaptive respiratory system disclosed herein; while FIG. 11 displays a block diagram of the diaphragm lung model of FIG. 10 coupled to the pattern generator/pattern shaper arrangement of FIG. 5. The ability to obtain desired lung volume by simulating stimulation of the diaphragm using an open-loop control paradigm versus a closed-loop adaptive controller was examined. The results, as illustrated in FIG. 12, are shown in graphical charts of a comparison of desired versus measured values in both an open loop controller and an adaptive controller.

Referring to FIG. 10, the Diaphragm-Lung (DL) model as illustrated in FIG. 10 may include two major components—a muscle model and a lung model. The physiological model may be based on a two mass, three spring, two dashpot model. The rib cage is represented on the left side of the block diagram and the abdomen is represented on the right side. $C_{AC}$ and $C_A$ represent damping coefficients, while $K_L$, $K_{AC}$, and $K_A$ represent spring coefficients. The model for muscle (including fatigue) may be based on the Macklem model for inspiratory muscle mechanics (which is incorporated by reference: Macklem et al., "A Model of Inspiratory Muscle Mechanics," Journal of Applied Physiology (1983)) and the muscle model with fatigue may be adapted from by the Hawkins and Hull model (which is incorporated by reference: Hawkins, David and M. L. Hull, "Muscle Force as Affected by Fatigue: Mathematical Model and Experimental Verification," Journal of Biomechanics (1993)). There are three muscles fiber types: (1) for slow twitch oxidative fibers, (2) for fast twitch oxidative glycolytic fibers, and (3) for fast twitch glycolytic fibers. The model assumes the same index of fatigue for the first and second muscle types. The percentage of the three fiber types in the lungs for an average person is used in the modeling of the diaphragm muscle and is incorporated by reference (from Levine et al, "Cellular adaptations in the diaphragm in chronic obstructive pulmonary disease," New England Journal of Medicine (1997)). In particular, the diaphragm may be a muscle model including fatigue, which is represented by the following equation:

$$Fm = \sum_{i=1}^{3} [(na_i)(Ff_i)(IF_i) + (n_i)(Fpf_i) - (n_i - na_i)(Fpf_i)]\cos\alpha$$

where,

Fm represents instantaneous muscle force;

i refers to the three types of muscle fibers;

$n_i$ represents total number of fibers in each fiber pool (shown in Table 1);

$na_i$ represents total number of active fibers in each pool;

Ffi represents instantaneous force generating capacity of a given fiber type (N);

Fpfi represents the passive fiber force created when fibers are stretched beyond rest length;

IFi is the index of fatigue; and

A is the instantaneous pennation angle (0°).

Another part of the model may represent the physiological model for the response of the lungs to diaphragm's contraction. As shown in FIG. 10, the block on the right represents the load on the diaphragm and its connection to the lungs. The block on the left represents the load of the lungs on the rib cage and its connection between the lungs and the rib cage. The dashpot and spring in parallel on either side of the blocks represent the physiological characteristics of soft tissue and muscle tissue that surround the abdominal cavity, which cause the movement of the cavity to be dampened and spring-like. The spring in the middle represents the connection of the lung tissue and the tendency of the lungs to return to their standard volume if no other forces are present. While this model cannot be used to accurately measure the amount of airflow in and out of the lungs, it approximates the response of the lungs to the displacement caused by contraction of the diaphragm. The important variable thus is the simulated "lung volume" or, more accurately, the displacement between the two blocks B1 and B2 representing the two sides of the lungs. This is the variable that is "measured" in the simulations. Assuming the position of box B1 on the left is $x_2$ and the position of the box B2 on the right is $x_1$, where they both have a mass of $m_2$ and $m_1$ respectively, the force equations equal:

$$m_1\ddot{x}_1 + C_{AC}\dot{x}_1 + (K_{AC}+K_L)x_1 = K_L x_2$$

$$m_2\ddot{x}_2 + C_A\dot{x}_2 + (K_A+K_L)x_2 = K_L x_1 + f_m$$

where fm is the force of the diaphragm muscle.

Accordingly, the transfer function for each $x_1$ and $x_2$ was derived and used in the implementation of the model.

Table 1 summarizes the percentages of each fiber for each diaphragm muscle type. Variable n1 represents slow twitch oxidative fibers; variable n2 represents fast twitch oxidative glycolytic fibers; and variable n3 represents fast twitch glycolytic fibers. As shown, fibers n2 and n3 fatigue more quickly. These values were obtained from the Levine et al. reference ("Cellular adaptations in the diaphragm in chronic obstructive pulmonary disease," New England Journal of Medicine (1997)), which is incorporated herein.

|  | Nominal Diaphragm |
| --- | --- |
| n1 | 46% |
| n2 | 39% |
| n3 | 15% |

Table 2 summarizes the parameters used for the diaphragm-lung physiological model.

|  | Nominal |
| --- | --- |
| n1 | 4600 |
| n2 | 3900 |
| n3 | 1500 |
| CAC | 0.5 |
| KAC | 1 |
| KL | 0.05 |
| CA | 0.01 |
| KA | 0.75 |
| m1 | 100 |
| m2 | 20 |

FIGS. 12A-D show graphical charts of the comparison of desired versus measured values in both an open loop controller and an adaptive controller, where the lung displacement and current supplied to the muscle are illustrated. In particular, FIGS. 12A-D display the comparison of the open loop controller and the adaptive PG/PS controller at cycles 1-8 and 201-208. In general, FIGS. 10-12D demonstrate the advantages of the adaptive controller over the open loop configuration. The open loop controller was programmed with a stimulation pattern that would give a similar lung volume trajectory to the desired one; wherein, the data for the open loop controller represents data correlating to the open loop controller of FIG. 1. The current max was then adjusted so that the measured trajectory closely matched the desired trajectory for the first few cycles. The open loop controller has the same stimulation current for each cycle, while the adaptive controller adapts the stimulation current to account for time-dependent variables such as fatigue.

The data for the adaptive controller represents data correlating to the PG/PS controller 100 of FIG. 3. In operation, the pattern generator portion may generate a set of waveforms that are used in timing, where these may also represent the base of the controllers output. Accordingly, the pattern shaper may adjust weights of these waveforms in order to produce the pattern of stimulation to the muscle/nerve in order to provide a trajectory closer to the desired one. In this study, the breathing pattern was set to a desired frequency; therefore, the calculations for the pattern generator in this set of experimental results were fixed. As a result, the pattern shaper produced a set of raised cosine waves at different time steps. The cosine waves were set such that one cosine wave would reach its peak at each time step during each cycle, since the controller may be updated at 25 Hz. That is, each time step was 40 ms and there may be 24 basis functions per cycle which last about 960 ms. The pattern shaper may modify the scale of each of these 24 cosine waves in order to allow for the adaptive output.

The stimulation for the adaptive controller was determined by the PG/PS control system and updated at 75 Hz. At cycles 201-208, it can be seen that the adaptive controller is closer to the desired trajectory, while the open-loop controller has faded to approximately 50% of the desired lung displacement. The parameters were set to represent an average person's diaphragm and lungs (nominal parameters). The top row of the panels shown in FIGS. 12A-D represents the lung displacement (LD), where the desired trajectory is shown as the dashed line and measured trajectory shown as a thick bold line during the first eight cycles (top) and cycles 201-208 (bottom) of a single 300-cycle trial. The bottom row of the panels displayed in FIGS. 12A-D illustrates the stimulation current supplied to the muscle model. The horizontal axis shows time in seconds, while the vertical axis shows the lung displacement of each breath in arbitrary units (on the top) and the current supplied to the muscle (on the bottom).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

Thereby, the foregoing description of various aspects of the device of the present application is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of adaptive pacing of muscles and nerves in a body, the method comprising:
   implanting at least one electrode in at least one tissue associated with controlling a breathing pattern frequency of a user;
   detecting, by a first feedback section having at least one sensor, at least one physiological parameter of the user;
   comparing, by a controller coupled to the at least one electrode and the first feedback section, the detected at least one physiological parameter with at least one desired physiological parameter to generate a first difference;
   generating, by a feed-forward section of the controller, a stimulus control signal for adjusting the breathing pattern frequency using the first difference;
   sending, by the controller, the stimulus control signal to the at least one electrode; and
   controlling, by the at least one electrode, movement of the at least one tissue in response to receipt of the stimulus control signal sent by the controller;
   the feed-forward section of the controller comprising a pattern generator coupled between a first comparator of the controller and a pattern shaper of the controller, the first comparator generating the first difference;
   the pattern generator comprising a first biomimetic design having a first neural network mimicking a simplified connectivity pattern of respiratory related neurons of a brain stem to produce the breathing pattern frequency;
   the pattern shaper comprising a second biomimetic design having a second neural network mimicking a simplified connectivity pattern of phrenic motor neurons that determines, based upon the breathing pattern frequency, at least one amplitude of at least one stimulus pulse and at least one frequency of the at least one stimulus pulse; and
   the pattern shaper generating the stimulus control signal including the at least one amplitude and the at least one frequency.

2. The method of adaptive pacing of muscles and nerves in a body according to claim 1, further comprising:
   generating, by a second feed-back section having at least one lung volume sensor, a sensed lung volume, the controller further comprising a second comparator coupled to a multiplier of the controller;
   receiving, by the second comparator, a scaling factor and the first difference to generate a second difference;
   generating, by the multiplier, in response to receipt of the second difference and a normalized lung volume, a desired normalized lung volume; and
   receiving, by a third comparator of the controller, the desired normalized lung volume and the sensed lung volume;
   generating, by the third comparator, a pattern shaper control signal for adapting the second neural network of the pattern shaper based on the difference between the sensed lung volume and the desired normalized lung volume.

3. The method of adaptive pacing of muscles and nerves in a body according to claim 2, further comprising generating, by the third comparator, a pattern generator control signal for adapting the first neural network of the pattern generator based on the difference between a measured lung volume and a desired normalized lung volume.

4. The method of adaptive pacing of muscles and nerves in a body according to claim 1, the at least one tissue comprising a muscle.

5. The method of adaptive pacing of muscles and nerves in a body according to claim 1, the at least one tissue comprising a nerve.

6. The method of adaptive pacing of muscles and nerves in a body according to claim 1, the at least one sensor comprising at least one of an associated on-body sensor, an in-body sensor, and an ultra-sonic sensing device.

7. The method of adaptive pacing of muscles and nerves in a body according to claim 1, the at least one physiological parameter comprising at least one of an end-tidal $CO_2$ level of the body, a transthoracic impedance between external or internal electrodes, chest wall motion, abdominal wall motion, phrenic nerve activity, blood pH, blood oxygen concentration, blood carbon dioxide concentration, blood pressure, activity level, body posture, phrenic nerve activity, airflow, heart sounds, sensed electrical activity, blood flow, and blood circulation time.

8. The method of adaptive pacing of muscles and nerves in a body according to claim 1, the at least one sensor of the first feedback section comprising at least one of an end-tidal $CO_2$ sensor, an arterial $CO_2$ sensor, a blood-oxygen level detector, and a capnograph.

9. The method of adaptive pacing of muscles and nerves in a body according to claim 1, the controller and the at least one electrode being coupled by a wireless data communication link.

10. A method of adaptive pacing of muscles and nerves in a body, the method comprising:
    detecting at least one physiological parameter of the body;
    comparing the detected at least one physiological parameter with at least one desired physiological parameter to generate a first difference;
    updating, by a pattern generator of a controller, at least one stimulation parameter in response to the first difference, the pattern generator having a first neural network mimicking a simplified connectivity pattern of bulbospinal neurons of a brain stem;
    generating, by the pattern generator, a breathing pattern frequency based on a first biomimetic pattern generated by the first neural network in response to the at least one updated stimulation parameter;
    generating, by a pattern shaper of the controller, a stimulus control signal comprising at least one amplitude of at least one stimulus pulse and at least one frequency of the at least one stimulus pulse, the pattern shaper having a second neural network mimicking a simplified connectivity pattern of phrenic motor neurons, and the generating of the stimulus control signal being based on a second biomimetic pattern generated by the second neural network in response to the breathing pattern frequency; and
    actuating, based on the stimulus control signal, an electrode coupled to at least one tissue of the body.

11. The method of adaptive pacing of muscles and nerves according to claim 10, the at least one tissue comprising a muscle.

12. The method of adaptive pacing of muscles and nerves according to claim 10, the at least one tissue comprising a nerve.

13. The method of adaptive pacing of muscles and nerves according to claim 10, the at least one physiological parameter comprising an end-tidal $CO_2$ level of the body.

14. The method of adaptive pacing of muscles and nerves according to claim 10, the at least one physiological parameter comprising at least one of a transthoracic impedance between external or internal electrodes, chest wall motion, abdominal wall motion, phrenic nerve activity, blood pH, blood oxygen concentration, blood carbon dioxide concentration, blood pressure, activity level, body posture, phrenic nerve activity, airflow, heart sounds, sensed electrical activity, blood flow, and blood circulation time.

15. The method of adaptive pacing of muscles and nerves according to claim 10, the step of detecting at least one physiological parameter of the body being performed by at least one sensor coupled to the controller.

16. The method of adaptive pacing of muscles and nerves in a body according to claim 15, the at least one sensor comprising at least one of an end-tidal $CO_2$ sensor, an arterial $CO_2$ sensor, a blood-oxygen level detector, and a capnograph.

17. The method of adaptive pacing of muscles and nerves according to claim 10, further comprising:
   multiplying a pattern generator gain factor by the first difference, the at least one physiological parameter comprising an end-tidal $CO_2$ level of the body;
   multiplying a pattern shaper gain factor by the first difference, the breathing pattern frequency being generated in response to the product of the pattern generator gain factor and the first difference;
   measuring an actual breath volume;
   receiving a scaling factor input;
   generating a second difference between the scaling factor input and the product of the pattern shaper gain factor and the first difference;
   multiplying the second difference by a normalized volume as a function of time to generate a desired volume as a function of time;
   generating a third difference between the measured actual breath volume and the desired volume as a function of time; and
   adapting the second neural network of the pattern shaper using the third difference.

18. A non-transitory computer-readable storage medium comprising computer executable program code stored thereon that, when executed by a processor, performs the following steps:
   detecting at least one physiological parameter of a body;
   comparing the detected at least one physiological parameter with at least one desired physiological parameter to generate a first difference;
   updating at least one stimulation parameter in response to the first difference using a pattern generator, the pattern generator having a first neural network mimicking a simplified connectivity pattern of bulbospinal neurons of a brain stem;
   generating a rhythmic breathing pattern frequency based on a first biomimetic pattern generated by the first neural network using the at least one updated stimulation parameter;
   generating a stimulus control signal using on a second biomimetic pattern generated by second neural network mimicking a simplified connectivity pattern of spinal cord neurons that determine at least one frequency of a stimulus pulse and at least one amplitude of the stimulus pulse, the generating of the stimulus control signal being based on the rhythmic breathing pattern frequency; and
   actuating an electrode coupled to at least one tissue of the body using the stimulus control signal.

19. The non-transitory computer-readable storage medium according to claim 18, the computer executable program code, when executed by a processor, further performing the following steps:
   detecting motion and at least one corresponding activity level;
   detecting changes in metabolic demand corresponding to the detected motion and the at least one corresponding activity level; and
   coordinating a magnitude of at least one stimulus parameter of the stimulus control signal to match the metabolic demand as indicated by the measured activity level.

20. The non-transitory computer-readable storage medium according to claim 18, the at least one tissue comprising a muscle, a nerve, or both, and
   the at least one physiological parameter comprising at least one of an end-tidal $CO_2$ level of the body, a transthoracic impedance between external or internal electrodes, chest wall motion, abdominal wall motion, phrenic nerve activity, blood pH, blood oxygen concentration, blood carbon dioxide concentration, blood pressure, activity level, body posture, phrenic nerve activity, airflow, heart sounds, sensed electrical activity, blood flow, and blood circulation time.

\* \* \* \* \*